(12) United States Patent
Cheng et al.

(10) Patent No.: US 6,569,133 B2
(45) Date of Patent: May 27, 2003

(54) URINE MANAGEMENT SYSTEM FOR HUMAN FEMALES

(75) Inventors: Gordon C. Cheng, Carlisle, MA (US); James R. Valentine, Reading, MA (US)

(73) Assignee: Uroscientific, Inc., Woburn, MA (US)

( * ) Notice: Subject to any disclaimer, the term of this patent is extended or adjusted under 35 U.S.C. 154(b) by 0 days.

(21) Appl. No.: 09/826,778

(22) Filed: Apr. 5, 2001

(65) Prior Publication Data

US 2001/0037097 A1 Nov. 1, 2001

Related U.S. Application Data

(60) Provisional application No. 60/195,040, filed on Apr. 6, 2000.

(51) Int. Cl.[7] .............................................. A61M 1/00
(52) U.S. Cl. ........................ 604/329; 604/327; 600/574
(58) Field of Search ................................ 604/329, 327, 604/544, 347, 349; 600/574

(56) References Cited

U.S. PATENT DOCUMENTS

| | | | | |
|---|---|---|---|---|
| 4,784,654 A | * | 11/1988 | Beecher | 604/329 |
| 4,813,943 A | * | 3/1989 | Smith | 604/329 |
| 5,053,027 A | * | 10/1991 | Manfredi | 600/574 |
| 5,147,301 A | * | 9/1992 | Ruvio | 600/29 |
| 5,411,495 A | * | 5/1995 | Willingham | 600/584 |
| 5,865,821 A | * | 2/1999 | Lowey | 604/329 |
| 6,342,049 B1 | * | 1/2002 | Nichols | 604/327 |

FOREIGN PATENT DOCUMENTS

| | | | |
|---|---|---|---|
| EP | 0 241 064 A1 | * 10/1987 | A61F/5/44 |
| WO | 91/04714 | * 4/1991 | |

* cited by examiner

Primary Examiner—Henry Bennett
Assistant Examiner—Alfred Basichas
(74) Attorney, Agent, or Firm—Dishong Law Offices

(57) ABSTRACT

A urine management system for human females comprising a novel collection device, a novel conveyance tube, and a novel storage container is described. The collection device is worn by the user in direct contact with the skin surfaces surrounding the urethral opening being held in place by an undergarment. The collector comprises a thin layer of pliable and water-permeable material through which leaked or voided urine passes and that is underlain by a layer of water-wicking material which may also contain one or more open channels for directing and conveying the flow of urine to a fitting connection with the conveyance tube. The conveyance tube, a novel thin-wall, flat tube, contains a spacer throughout its length to prevent the tube lumen from being completely closed and sealed off by kinks or twists in the tube. The tube can conform to the body shape of the wearer, expands as flow rate increases, and shrinks and flattens as flow drops off. Urine is retained as physically stabilized material in a storage container that can be either replaced and disposed of or emptied and reused with cleaning as needed. Physical stabilization of the fluid urine is accomplished using an absorbent or gel-forming material. The storage container's internal structure also provides a means for unique fluid transfer and retention capabilities. To form the entire system, the devices are serially and contiguously connected to form a continuous liquid pathway that enables removal of residual pools of urine, as well as transport and storage of urine at locations higher than the source.

38 Claims, 10 Drawing Sheets

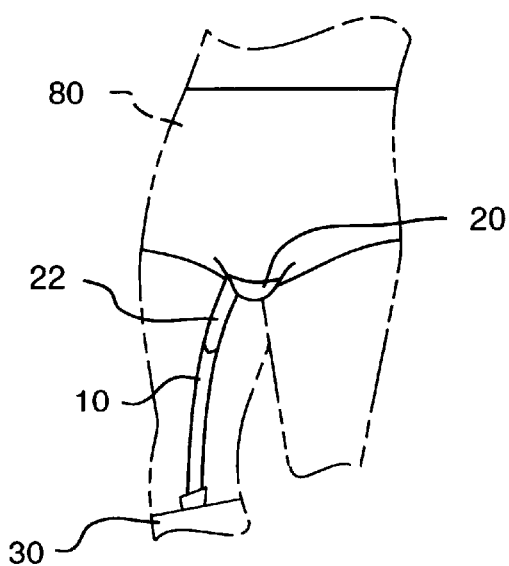
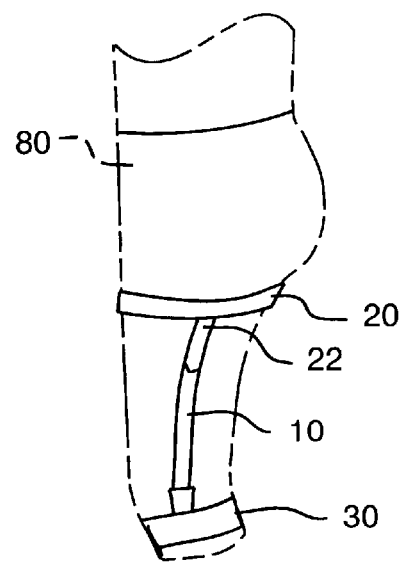
FIG. 2A          FIG. 2B
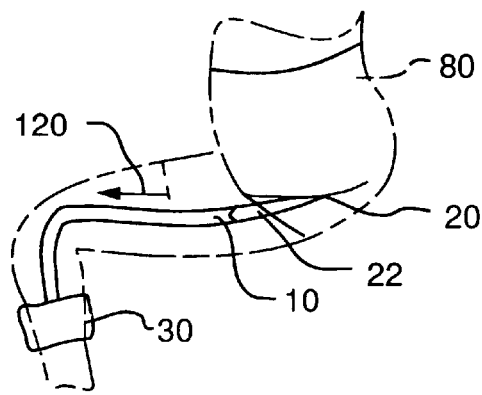
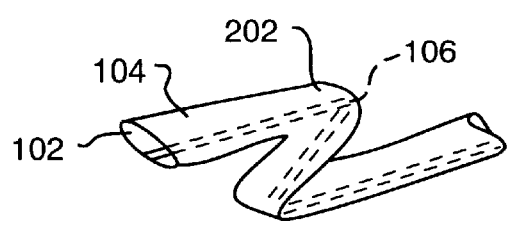
FIG. 2C          FIG. 3

URINE MANAGEMENT SYSTEM FOR HUMAN FEMALES

CROSS-REFERENCE TO RELATED APPLICATIONS

This application claims benefit of the filing date of Provisional Application Serial No. 60/195,040, filed on Apr. 6, 2000, for URINE MANAGEMENT SYSTEM FOR HUMAN FEMALES.

BACKGROUND OF THE INVENTION

1. Field of the Invention

The present invention relates to the field of collecting urine and conveying it from point of collection to storage. More particularly, this invention relates to an apparatus for urine collection from a female human, storage, and disposal, and that addresses the problems associated with such devices of current art. Most particularly, this invention relates to an apparatus that addresses the problem of female human incontinence.

2. Description of Related Art

Urine incontinent human females whose condition does not require use of an internal or "indwelling" catheter are faced with two alternatives to manage their condition: using a system of devices worn on the body to collect and to store the urine separately for periodic disposal, or wearing an absorbent garment (also including pads and diapers) that collects and stores the urine in the crotch area for periodic changing. For some individuals, the system of devices alternative may be preferable to the absorbent garment alternative because of various personal and social reasons. Such systems of devices consist of separate devices for urine collection, conveyance to storage, and storage. Several urine management systems for females have been described in the prior art using collection devices constructed for female anatomical needs, and conveyance tubing and leg bag technology that are essentially similar to those used for males. Despite the number of such ideas and patents, no devices or systems intended for females are commercially available at this time, suggesting that the prior art devices have not proven to be practicable or practical vis-a-vis the abundant range of absorbent garment products commercially available for incontinent human females.

All prior art urine collectors for females are configured as cups, pouches, bags and cones, and span the range of coverage from the entire vulval area to simply the urethral opening. All such devices require a tight seal between the body and the device. To achieve this seal, some make use of adhesives, together with pliable foam or similar materials.

Prior art collectors require connection to some form of external storage device. In some cases, the collectors are integrated with, or permanently attached to, the urine storage device. Other collectors, which are detachable from the storage devices, use conventional rubber tubing All prior art urine collectors for females are configured as cups, pouches, bags and cones, and span the range of coverage from the entire vulval area to simply the urethral opening. All such devices require a tight seal between the body and the device. To achieve this seal, some make use of adhesives, together with pliable foam or similar materials.

Prior art collectors require connection to some form of external storage device. In some cases, the collectors are integrated with, or permanently attached to, the urine storage device. Other collectors, which are detachable from the storage devices, use conventional rubber tubing for connection. Appendages to collection devices used for transporting urine away are susceptible to crimping which could block the discharge of urine.

Prior art collectors for females use either gravitational flow or a wicking mechanism to transport urine away from the discharge area. Thus, these collectors are unable to move urine along an ascending flow path from the point of discharge to a leg-mounted storage bag. This situation is especially problematic when the user is seated. Instead of draining, urine will pool in the collector risking overflow and embarrassment. In addition, prolonged skin exposure to urine and urine decomposition products (e.g. ammonia), can cause skin injury, breakdown, and infection.

Urine conveyance tubing generally makes use of small-bore rubber tubing. For a female urine management system, it would be desirable if the tubing is comfortable for skin contact, minimally visible under clothing, and sufficiently resistant to crimping, kinking, or other types of flow blockage resulting from body movements. To provide kinking resistance, prior art devices resort to using heavy wall thickness, relatively rigid materials, internal protrusions molded into the tube's inner wall for preventing the tube wall from collapsing or incorporating axial pleats or convoluted tube walls for guiding the bends. All these prior art techniques fail to satisfy the need for the user's comfort.

In addition to the collapse of the tube lumen, flow blockage in prior-art conveyance tubes can also result from formation of liquid slugs when displaced air from the storage device is prevented from uprising in the narrow bore. While venting the storage device circumvents this problem, it emits unpleasant odor.

The simple use of a thin-walled tube in place of the thicker-walled urinary tubing in current use could result in a poorer performance with respect to collapsing and sealing off of periodic, low volume flows such as urine incontinence leakage. While any open tube may be used as a conduit for gravity flow, to provide active fluid transport in an ascendant path to a higher point prior to reaching the descendent path, as in the situation of a seated user, urine flow needs to proceed from the urethral opening up the thigh to a higher point near the knee and then flow "down" to a storage container attached to the lower leg. A simple open tube will not work.

In the prior art, the storage device is normally a flexible-wall reservoir that is either attached to the user's leg or suspended from the waist. These reservoirs are made from heavy-gauge sheeting of latex rubber, vinyl, or similar polymer with a single storage chamber. All containers are provided with outlet valve to allow for periodical draining. In addition, the containers must be cleaned and disinfected regularly to avoid odor and buildup of bacteria. However, most urine containers are discarded after 1–2 weeks because they cannot be thoroughly cleaned.

In single-chamber flexible wall storage devices, collected urine accumulates at the bottom to give a localized bulge under clothing, which is visible and impedes movement of the wearer. The contained liquid tends to slosh around when the wearer moves creating noise and a disconcerting feeling. There are some prior art baffles or other internal attachments between the walls to reduce the wall bulging and the liquid sloshing; however the overall container still bulges. In addition, if the storage device becomes accidentally disconnected, the spill of contained liquid urine can be very messy. As mentioned earlier, all prior art storage devices require venting of urine-displaced air, which emits an unpleasant odor.

Storage devices containing liquid-absorbent materials such as gel-forming polymeric absorbents, are found in the prior art. In general, the prior art describes liquid absorption and gel formation in a single chamber envelope or bag with an inlet and containing a gelling agent or absorbent either in a highly confined mass or in an undefined shape. No provisions are described for deliberate distribution or mixing of the fluid to ensure rapid wetting and gel formation, nor are any provisions made for ensuring a particular shape or form of the absorbed or gelled fluid other than noting the geometric shape of the envelope or bag. Moreover, placement of unconfined dry solids such as these absorbents in a bag with angular corners often results in accumulation in one corner or along one edge as a result of settling and movement during shipping and handling.

Storage devices that take the form of leg bags rely on elasticized straps around the calf or suspension from a waist belt to maintain a desired position on the leg. Putting on these straps is tedious and time consuming. In addition, an improperly fastened leg bag may be more easily dislodged from the secure fastened position with consequent possible urine spillage.

One approach described in prior art to reduce localized bulging and liquid sloshing in storage devices is to immobilize the liquid into suitable absorbents either in confined porous packages or distributed as solids in an undefined distribution. These approaches are subject to potential blinding and blocking that will result in unpredictable liquid uptake performance and under-utilization of absorbent. Blinding, a physical characteristic of many absorbents, results from the formation of an outer shell of liquid-saturated material encapsulating the unused absorbent in the core. Such partially- or incompletely-blocked absorbent materials take up additional urine at a much slower rate than the dry materials. Blocking is the prevention of urine passage to other regions of the device by lumps of partially saturated absorbent.

If the user of this type of storage device is able to periodically discharge a strong stream of urine, the force of the urine jet is sufficient to mix the absorbent to prevent blinding. On the other hand, a constant dribble flow of urine from a heavily incontinent person would not be sufficiently energetic to overcome the blinding, resulting in excessive free liquid in the device. These prior art storage devices containing absorbents, which are intended for healthy users, are not adequate for incontinent persons.

From the above, it is clear that the current-art technologies and products available to incontinent individuals who wish to use a system of devices to meet their personal urine management needs are inadequate. Improved means for collecting, conveying, storing, and ultimately disposing of urine are needed. None of the prior art completely meets the objects of providing the following for ambulatory incontinent human females.

Urine collection and storage devices that accommodate the problems of ease of application, removal and changing.

Urine conduit devices that can be worn unnoticed, thus preserving privacy.

Urine collection, conveyance and storage devices that offer minimum potential for embarrassing leakage.

Urine storage devices that afford a convenient, discrete, and sanitary means for disposing of collected urine.

Skin contact surfaces of the collection device that are formed from materials that conform to the anatomical surface contours of the user to an extent sufficient to ensure that the device surfaces can be placed in contact with droplets or pools of urine liquid that may have been transferred to other skin surfaces during urine voiding or leakage.

Novel collection device that incorporates means for quickly transporting urine via capillary wicking flow supplemented, as needed, by temporary absorption in suitable absorbent media and by flow or temporary confinement in open channels to a connection with a conveyance tube conducts the urine to a urine storage package.

Thin-walled, flat tube that conducts urine from collection to storage and that expands only when conducting urine flow, and contains a spacer means to prevent crimping blockage of flow.

Wicking mechanism within the collector tube and system that draws the fluid up to a point of collection that is higher than the source.

Wettable surfaces and continuous wicking in collection and conveyance system that enable more complete and effective removal of urine wetness and products injurious to sensitive skin.

Regions in the wicking flow path of each device that can be treated with suitable antibacterial materials limit bacteria growth.

Thin, flat, multicompartment storage package that gives more uniform weight distribution than the prior art liquid leg bag, expanding open only as it fills with urine.

Tubing and storage package that can be attached to leg or clothing.

Single-use storage package made of lightweight, thin polymer film that is waterproof and gas-tight ensures cleanliness and eliminates odor.

Storage package that minimizes movement of immobilized, stored liquid when the wearer moves.

Storage package that is disposable as solid sanitary waste.

Storage package that has no vent or drain valve, thus avoiding significant sources of accidental leakage in liquid storage packages.

BRIEF SUMMARY OF THE INVENTION

To overcome the limitations of the prior art and to achieve the foregoing and other objects, and in accordance with the purposes of the present invention as described herein, an improved urine management system for incontinent human females is disclosed. The improved urine management system is formed by the serial connection of functional devices comprising a urine collector, a conveyance device, and a storage device. The system provides collection of incontinent urine leakage, conveyance of collected urine to the storage device where it is immobilized and stored prior to disposal a sanitary waste.

The urine collector collects and conducts away discharged urine for the purpose of removing that urine from the human female anatomical surface where urine discharge occurs to a storage device that is positioned in a physically separated location. The collector is not intended for retention of any substantial volume of collected urine, and any retention of urine in the collector is transitory in the sense that it is being conveyed to a storage devise positioned in a physically separate anatomical region. The collector has three principal functional parts: (a) a urine-intake layer to receive discharged urine and to transfer that urine to an underlying transport means; (b) a urine-impervious wall layer that encloses the non-body contact side of the urine-intake layer and is in sealed contact with the periphery of that urine-intake layer, and (c) a urine-transport means that is located in the internal region between the intake surface and the urine-impervious wall and that receives urine from the urine-intake surface and transports that urine away by means of either or combination of bulk flow and wicking transport from that intake surface to a point of connection with a storage device or conveyance tube.

The urine-intake layer has within it a layer of a material that is hydrophobic and that has openings that enable passage of urine from the body-contact side away from the body while inhibiting passage of urine in the opposite direction. The body-contact surface of the urine-intake layer enables imbibing of urine wetting the skin in the vicinity of the urine-discharge surface area as well as of droplets or streams of discharged urine. At least the urine-intake layer of the collector is made from materials that are substantially conformable to the urine-discharge anatomical surface of a human female.

The perimeter of the collector body-contact surface is urine impermeable and pliant to provide a barrier to urine leakage beyond the confines of the collector. The collector can be of several shapes so as to enable it to be held in place next to the skin either by an article of clothing or by its own shape when equipped with fastening means to hold such shape, and does not require additional manual pressure to hold it in place in order to achieve urine collection that is substantially free from leakage.

The urine transport means of the collector may be made from materials capable of wicking, such as needled felts, mats or bundles of rayon or cellulose acetate fiber or other capillary-containing material including fabrics, or open cell foams having an integrated waterproof coating on the outer walls that can convey and wick urine. The urine transport means can also be made from non-porous film materials whose interior surfaces have been previously coated with materials having the required wicking properties that can also wick and convey urine.

For the purpose of describing devices included in the present invention, wicking is defined as the flow of fluid through a bed of fine, interconnected capillary space, which will spontaneously imbibe, (hence wick) a fluid that effectively wets the walls of those capillaries. If the wick is on a level plane, it will continue to take up the liquid until all the spaces are filled or until the liquid reservoir is empty. Once filled, the wick will form a "drip" from the lowest point responding to gravitational forces. In addition, as a result of the capillary wicking action, a wetting fluid can travel "up" into narrow-diameter capillaries a distance of several centimeters in ascendant flow against the force of gravity. The height of this "capillary rise" is governed by the size and wetting properties of the capillaries and the properties of the liquid. If the as-yet-unwetted upper portion of a liquid-imbibing capillary wick is bent to a horizontal or a downward direction at a point below the maximum capillary rise, then the wick will be filled with liquid. If the wick is extended in a downward direction to a point below the level of the liquid reservoir, then descending flow of the liquid, induced by gravity, will empty the reservoir to the level of the wick inlet in a siphoning action. Thus, the wick can provide the necessary fluid "lift" via the capillary wetting function to commence the siphoning action. Separate components of the urine management system that contain wicking and that are placed in contiguous connection of wicking liquid flow path through the system allow the removal of leaked urine from the user through a conveyance tube to a storage device located outside of the crotch area, even when the user is in a seated position.

The width, thickness, and material of the urine transport means are selected to accommodate the expected maximum urine discharge flow rate of a given application. For example, the application could be for receiving a sudden discharge of a full bladder of urine of a normal human, or the application could be for receiving leaked urine from a completely incontinent person. In addition to containing the wicking layer, the urine-transport means also contains one or more open channels that can act as transitory reservoirs for urine flows whose volume temporarily exceeds the capillary volume of the fluid transport means and that also can conduct such contained excess liquid urine to the point of connection with either a storage device or a conveyance tube.

A portion of the collector can be extended beyond the immediate vicinity of the urine discharge anatomical surface so as to enable convenient connection to a separately located storage device. This so-called distal portion, or extension, of the collector is constructed in the shape of, or in use becomes the shape of, a flat tube and contains a spacer to prevent the walls of that tube from becoming sufficiently crimped so as to prevent draining of urine. The spacer may also be constructed from the same or different material as the urine transport layer or may be a physical extension of the urine transport layer. The distal portion of the collector may be connected through mating fittings that enable the connection of wicking continuity to the conveyance tube, or directly to a storage device using the same type of wicking connection. In this latter case, the conveyance tube becomes an integral extension of the distal portion of the collector without need for any intermediate connecting fittings.

The conveyance tube is an open tube for conveying urine from a urine collection device to a separately located urine storage device. The conveyance tube has, located throughout the length of its lumen, a spacer, which is a continuous length of a physical structure that serves to prevent the tubing lumen from becoming completely closed by crimping or other actions that result from movement of the human wearer. The two ends of the flat thin-walled conveyance tube can be fitted with suitable adapters to enable connection to collection and storage devices. The spacer having a finite thickness and width dimensions is produced by a variety of manufacturing processes, kc and is not totally or continuously attached to the tube wall and is not a protrusion molded into to the tube wall. The spacer may be made from various types of materials including woven materials (e.g., loosely knitted nylon, polyolefin, glass or metal fibers, textiles, etc), non-woven materials (e.g. rayon acetate needled felts, cellulose acetate fiber bundles, etc.), and flexible foams or solids (e.g., polyolefin film strips, polyolefin foam strips, silicone shapes, etc), depending the functionality desired of the conveyance tube in specific applications. The width, thickness, and material of the spacer are selected to accommodate the expected urine flow rate of a given application.

In addition to its function to prevent liquid blockage by a crimping action, the spacer of the conveyance tube may possess the physical property of wicking which is brought about by the use of urine wettable materials either they are inherently wettable or made wettable by a chemical or physical treatment. A spacer is selected with desired width, thickness, and material to accommodate the expected liquid flow situation. Wicking can promote the flow of urine from one point to another in the system. The connections of the conveyance tube have means to establish wicking-continuity with the urine collector and the urine storage device, if they are equipped with wicking connections.

The lumen of such conveyance tubes may have a variety of geometric shapes, and more preferably will, have the shape of a flat or partially flattened tube. The conveyance tube is constructed of a single or of multiple layers, at least one of which is urine-impervious, of thin materials, such as thin-walled plastic films, that are substantially conformable to the anatomical surface contours of a human female in the region between the outlet of the urine collection device and the inlet of the urine storage device. The thickness of the conveyance tube film layers may be in the range 0.0127 to 0.127 mm (0.0005 to 0.005 inch) and preferably in the range of 0.025 to 0.076 mm (0.001 to 0.003 inch), which is thinner by orders of magnitude than that of the rubber or polymeric elastomer tubes used with current urine management systems (typically in the range of 1.7 to 3.3 mm (0.067 to 0.13-inch)).

Multiple layers of thin films that are substantially unbonded can slide independently over one another thus retaining the flexibility of thin films while providing added mechanical protection for the urine-carrying tube elements. The exterior circumference of the conveyance tube may be formed as a continuous enclosure as may be resulted from manufacturing methods such as extrusion or by blow molding or could formed by joining the edges or areas proximal to the edges of two separate stripes of the same material by welding or adhesive substances.

The "flat" property of such flat conveyance tubes can be characterized as having a thickness-to-width ratio (i.e., the ratio of the minor-to-major axes of the ellipse formed by the cross-section of the partially flattened tube) of from less than 1.0 to a low value limited only by the thickness of the spacer, and preferably in the range of 0.05 to 0.5. Such thin-walled, flat conveyance tubes are considerably more flexible than the current thick-wall tube in conforming to fit contours of the human body. Thin-wall tubes may be most conveniently deployed in a "nearly-flattened" form that will "inflate" when free liquid passes through them and then return to the "nearly-flattened" shape when flow subsides. This flat or flattened conveyance tube has two exterior surfaces, and the tube may be positioned in such a way that one exterior surface lies proximal, and the other lies distal, to the skin of the user. An outer layer may be added to the either or both exterior surfaces of the conveyance tube that is made from the same materials of the conveyance tube or from different materials to suit different purposes (e.g., both may be made from soft, breathable materials, one may have a fastening means such as a temporary adhesive for fastening the tube to skin or to clothing, etc). The conveyance tube may be constructed so as to provide and enable multiple, simultaneous connections to multiple storage devices.

A collapsible conveyance tube for conveying liquid, having an interior cavity, an interior surface defining the cavity, and walls, is disclosed comprising a means for spacing that is substantially removably disposed within the interior cavity. The means for spacing prevents complete collapse of the conveyance tube. The means for spacing comprises a material selected from a group consisting of loosely knitted nylon fibers, loosely knitted polyolefin fibers, flexible solid shapes of polyolefins, flexible solid shapes of silicone rubber, loosely knitted fiberglass, loosely knitted aluminum, polyolefins film, porous wicking materials including needled felts of rayon and cellulose acetate fiber bundles, natural woven fabrics, and synthetic woven fabrics. The walls comprise material selected from a group consisting of rubbery polymer such as silicone rubber, latex rubber, elastic or elasticized fabric coated, polyolefins, latex, and polymeric. The means for spacing is positioned within the interior cavity to prevent the conveyance tube from crimping sufficiently to block drainage of the urine and comprises a wicking material to enable fluid transfer through the capillaries of said wicking material. The interior surface is selected from a group consisting of wettable materials and non-wettable materials that have been subjected to surface treatments to render the interior surface wettable for holding liquid.

The storage device receives, immobilizes and stores urine that has been conveyed from a separate urine collector located at the region on human female anatomical surface where urine discharge occurred. The storage device receives urine through a single inlet opening that is connected on to a urine conveyance tube or to a urine collection device. The urine storage device immobilizes received urine through one of more means of distributing the urine into predetermined locations within the device and rapidly converting the distributed urine to a form (solid, gelled-solid, or absorbed in capillary spaces) that no longer exhibits fluid properties. When the desired load of urine has accumulated in the storage device, the device can be detached from the connection with the collector or conveyance tube and, if desired, the connection opening on the device can be capped or covered. Subsequently, the used device along with the stored urine can be disposed of in a proper manner as a solid waste.

The storage device has four principal functional components: (a) an outer shell of a material that is impervious to urine liquid, that is sealed liquid-tight along all peripheral edges except for the inlet connector opening, and that is sized and configured to allow for expansion as needed when urine is being received for storage; (b) a urine-distribution means that uses either one or a combination of gravity-driven and capillary-wicking fluid transport forces to distribute received urine more or less uniformly throughout the immobilizing matrix of one or more absorbents; (c) urine-immobilizing absorbent means that, prior to contact with urine, is held in place as a matrix and that may consist of any combination of natural or synthetic fibers, cellulose fibers, water-absorbing natural or synthetic materials, shredded paper; (d) a single inlet connector that provides connections for both wicking continuity and bulk fluid flow from the conveyance tube to the urine distribution system in the storage device.

The outer shell of the storage device is constructed of a single layer or multiple layers of plastic films, each layer having a thickness is in the range of 0.013 to 0.25 mm (0.0005 to 0.010 inch) and each layer having a thickness preferably in the range of 0.025 to 0.10 mm (0.001 to 0.004 inch). Multiple layers of thin films that are substantially unbonded can slide independently over one another to retain the flexibility of thin films while providing added mechanical protection for the urine-contacting surfaces. When lying flat, the storage device has two exterior walls, One or both of which may be covered with a layer of soft breathable material.

The urine distribution means consists of a wick throughout its working length in one or more predetermined locations within the device and a fluid distribution channel formed between a barrier film and the wick. Transfer of the urine from the wicking material to the absorbent can take place in one of two ways: either by bulk flow or by a "bridging" transfer to the absorbent matrix brought about by close physical proximity of the wick to the matrix of absorbent or absorbents. The wick lie within or in contact with a barrier film that distributes urine to predetermined locations of absorbent matrix. Urine to be absorbed is conveyed by wicking, either alone or in combination with bulk flow of urine in fluid pathways adjoining the wick, into the immediate vicinity of unused or partially used absorbent material.

Liquid distribution and absorption regions may be placed adjacent to each other in the storage device. A thin film barrier wall that has flow-limiting properties may be used to provide separation of the urine distribution channels in the liquid distribution region and the urine immobilization matrix in the liquid absorption region. A barrier film may achieve the flow-limiting objective by having an array or arrangement of small penetrations, or by possessing the property of urine permeability in selected areas. The barrier films can be selectively permeable to the urine in some or all regions in place of some or all of the arrayed penetrations. Any excess liquid urine that begins to accumulate near a penetration will tend to induce urine movement through the fluid pathway to another penetration region that can accommodate the flow. The number of holes and their spacing is predetermined for each application based on expected flow. The barrier can be positioned between a distribution channel and the layer of absorbent materials, or wrapped around a distribution channel that is surrounded by absorbent, or layer wrapped around a mass of absorbent that is surrounded by a distribution channel or network of channels. A wicking medium having a surface condition that tends to limit the penetration by the absorbent materials, whether dry or wetted with liquid, into the interior of the wicking medium will also accomplish the same limiting and distribution function. An absorbent or liquid-imbibing material having a surface condition that tends to limit the penetration of liquids to be absorbed or imbibed into the interior of the absorbent or imbibing material will also accomplish the same limiting and distribution function.

The matrix of immobilizing materials accommodates physical distribution of immobilizing materials and holds them in pre-determined locations within the storage device, and urine is distributed in a pre-determined manner so as to enable a more uniform volume expansion of the immobilizing materials as urine is absorbed. The purpose of this distribution is to minimize localized bulging of the storage device, as an example, at the bottom of the device. Urine distribution is accomplished by using a material that possesses the property of wicking. The matrix of immobilizing materials can be located in one or more compartments within the storage device. If there are multiple compartments, they are connected together with distribution channels to convey the urine to the absorbent. The matrix of immobilizing materials may be in a form of a physically mingled mass of non-woven fibers with one or more absorbents, or as one or more solid absorbent materials held in or on a physical structure such as a woven textile or non-woven mat of fibers, or as one or more absorbent materials coated onto the surface of the compartment wall in partially gelled form or by suitable attachment means, or as a material suitable for confining liquids by capillary force, or a combination of the above. In addition, one or more absorbent materials may be placed in the compartment or compartments in loose form provided that the number and shape of the compartments and the liquid distribution means are such that the liquid will be distributed more or less uniformly to the overall mass of absorbent. Absorbent materials include, but are not limited to, hydrophilic polymers formed from a variety of synthetic polar polymeric materials such as gel resins polyacrylamide and polyacrylic acid, $Na^+$ salt, synthetic polar polymeric materials chemically combined with natural polymers such as polyacrylic acid $Na^+$ salt on starch; synthetic polar polymeric materials physically combined with fibrous materials such as gel resin fine particles in paper fiber matrix, inorganic compounds that react with aqueous liquids to form solid hydrate compounds such as silica gel and calcium sulfate; organic fiber masses, both woven and non-woven, including cellulose fiber, needled felt pads, absorbent paper.

The external appearance of an unused storage device is of a thin, flattened form that expands more or less uniformly in thickness as it fills with urine. The storage device can be positioned, and that position maintained by any of a number suitable means (including the use of straps, adhesive tape, loop-and-hook fasteners, or in the pouch or pocket of apparel, among other ways), on several locations on the body of the human female user, e.g., on the calf or thigh in a wrap-around or substantially wrapped-around orientation, at the hip, etc. In addition, the device may be attached to the clothing of the human female user or may be attached to a nearby article, e.g. a wheelchair, bed, chair, etc. It can be worn attached to the user's body, e.g., worn on or around a leg, or attached to clothing. The storage device connects securely with a collection device directly or through a conveyance tube, and so is suitable for an ambulatory incontinent human when attached to the leg or waist or when attached to clothing at suitable points, and by a non-ambulatory human when attached to a suitable location in her immediate vicinity.

The storage device may be constructed so as to exclude entrapped air, thus enabling an unused device to have a volume somewhat less than that of an unused device that contained entrapped air. The ability of the storage device to exclude entrapped air also avoids the need to vent air that is displaced when urine is admitted into the storage device. The storage device is disposable.

Accordingly, it is a primary object of the present invention to provide a urine management system for human females that is comprised of a collection device, a conveyance tube, and a storage device, that accommodates ambulatory use, and that, in particular, addresses the problem of incontinence, overcoming the above-described limitations and disadvantages of the prior art.

A specific object of the present invention is to provide a urine conveyance tube that is readily conformable to human body contours and motions and that will reliably conduct the flow of urine without blockage. This tube connects a urine collection device with a urine storage device.

A further object of the present invention is to provide a urine conveyance tube that that can collapse to a flatter geometry when no fluid urine is in the lumen of the tube, and yet can also easily change in internal shape and dimensions so as to accommodate simultaneous, countercurrent flow of urine and atmospheric gases internal to the urine collection and storage devices.

A still further object of the present invention is to provide a urine conveyance tube whose internal lumen contains along its entire length a separating body that prevents complete blockage of fluid flow due to kinking, crimping, or otherwise collapsing.

A yet still further object of the present invention is to provide a urine conveyance tube that can, when desirable, accommodate ascending flow of urine, overcoming the force of gravity for a finite distance.

A yet still further object of this invention is to provide a urine conveyance tube that will have capability for limiting the growth of microbial organisms in that urine by maintaining antibacterial conditions at one or more locations along the urine flow path within said tube.

A yet still further object of the present invention is to provide a set of one or more devices for connecting this novel urine conveyance tube with novel collection devices and novel storage devices. These connecting devices can be combined with combinations of the novel urine conveyance tube and other urine handling devices to form kits of devices from which various urine management systems for incontinent individuals may be constructed.

A yet still further object of this invention is to provide an easy-to-use, secure, minimally protruding and comfortable means to store urine that has been conveyed from a urine collection means.

A yet still further object of this invention is to provide a urine storage container that is readily adaptable to human body contours and movements, and that will reliably absorb urine conveyed to it, converting the urine to a form in which the urine no longer has liquid-like flow properties.

A yet still further object of the present invention is to provide a urine storage container that will provide a more uniform weight distribution than current urine storage leg bags. The container may be provided in flattened configuration, which expands open only as it fills with urine. The container may be attached around the leg, worn attached and hanging from the waist, or worn attached to clothing.

A yet still further object of the present invention is to provide a urine storage container that can be shape-fitted around a limb and that can be self-tightening to maintain position as said container fills with urine.

A yet still further object of the present invention is to provide a storage container containing an absorbent or gel-forming polymer that will, when contacted with the conveyed urine, become partially or wholly filled with absorbed or gelled liquid that does not move or flow like a liquid when the container wearer moves.

A yet still further object of the present invention is to provide a storage container that will convey and distribute liquids to be absorbed such as urine by wicking or other distributive means into the immediate vicinity of unused or partially used absorbent material so as to facilitate fluid transfer to said absorbent materials which are intended to absorb that increment of liquid.

A yet still further object of the present invention is to provide a storage container that will have the capability for limiting the growth of microbial organisms in that urine by maintaining antibacterial conditions at one or more locations along the urine flow path within said storage container.

A yet still further object of the present invention is to provide a single-use storage container that may be made of lightweight materials. Without the need to withstand multiple cycles of cleaning and reuse, the wall structure of the storage container does not need to be especially heavy or rugged. A single-use storage container eliminates the need for cleaning and assures cleanliness.

A yet still further object of the present invention is to provide a storage container that, together with its content of absorbed or gelled urine, can be disposed of as sanitary solid waste.

A yet still further object of the present invention is to provide a storage container in which no drain opening for liquids is needed, thus avoiding that significant source of accidental leakage from liquid storage containers.

A yet still further object of the present invention is to provide a storage container that will facilitate absorption of liquids delivered from other storage containers.

A yet still further object of the present invention is to provide a set of one or more devices for connecting this novel urine storage container with currently existent devices for collecting, conveying, and storing urine. These connecting devices can be combined with combinations of this novel urine storage container and existent urine handling devices to form kits of devices from which various urine management systems for incontinent individuals may be constructed.

A yet still further object of the present invention is to provide an easy-to-use, secure, leak-free, minimally visible, and health-promoting urine collection device for human females.

A yet still further object of the present invention is to provide a urine collection device for human females that is easy to put on and remove, that provides a urine-resistant leak seal, and that will reliably transfer urine emitted from the urethral opening to a conveyance device for transfer to storage.

A yet still further object of the present invention is to provide a urine collection device that will remove residual drops and pools of urine, especially those in contact with the users skin, and will promote the exchange of atmosphere next to the skin, thus promoting the health of those skin surfaces.

A yet still further object of the present invention is to provide a urine collection device for human females that can be easily and conveniently applied to the anatomical area.

A yet still further object of the present inventions is to provide a urine collection device for human females that will remove any freestanding pools or drops of urine the collection device and transport that urine to the conveyance tube for removal.

A yet still further object of this invention is to provide a urine collection device that will have the capability for limiting the growth of microbial organisms in that urine by maintaining antibacterial conditions at one or more locations along the urine flow path within said collection device.

A yet still further object of the present invention is to provide means for connecting the urine collector with currently existing devices for conveying and storing urine.

A yet still further object of this invention is to provide enhanced capability to remove residual liquid urine that is not removed from the collection device and the conveyance device by gravity drainage. Removal of this residual urine will minimize excessive exposure of skin to the moisture and decomposition products from this residual urine can result in injury to that skin.

A yet still further object of this invention is to provide a novel urine management system that will have capability for gathering residual urine and for limiting the growth of microbial organisms in that urine, thereby minimizing the potential for introduction of any system-generated microorganisms into the urinary tract of the user. By facilitating the gathering of isolated pools of residual liquid urine into the wicking, and by maintaining antibacterial conditions at one or more locations along the urine flow path within said management system, both the growth of such infectious agents and transport into the urethral region will be discouraged.

A yet still further object of this invention is to provide for serially-connecting the novel devices for collecting, conveying, and storing urine such that the several contiguous connections of wicking and wetting components are maintained.

A yet still further object of this invention is to provide a system for collecting, conveying and storing urine from human females comprising a collection means, a means for conveyance between collection and storage, and storage means wherein the collection means is a flexible body or housing that incorporates means for confining and imbibing urine which exits the urethral opening, and means for transporting the urine to a conveyance tube that will conduct the urine to a urine storage device.

A yet still further object of the present invention is to provide a means for wicking urine from one location to another, said wicking means may be a physical structure separate from the extension, may be a physical structure attached to the tube, or may be formed on the tube wall itself through selection of a wettable material for the tube wall or by treatment of the tube wall.

A yet still further object of the present invention is to provide a means for wicking urine to remove pools and droplets of urine from the interior of the extension.

A yet still further object of the present invention is to provide a means is for conveyance of urine wherein a conveyance tube that is connected to the urine collecting means and to the urine storage means contains a means for wicking urine from one location to another. Said wicking means may be a physical structure separate from the conveyance tube, may a physical structure attached to the tube, or may be formed on the tube wall itself through selection of a wettable material for the tube wall or by treatment of the tube wall.

A yet still further object of the present invention is to provide a conveyance means wherein the conveyance of urine is accomplished in a flat, thin-walled tube that is connected to the urine collecting means and to the urine storage means, said flat, thin-wall tube remaining in a collapsed, flattened configuration except when fluid is present within the lumen of the tube.

A yet still further object of the present invention is to provide a flat, thin-walled conveyance tube that contains within the length of its lumen a structure, either separate from or connected to the wall of said tube, a means to prevent the lumen of said thin-wall tube from becoming completely closed to the flow of urine when said tube is crimped, folded back upon itself or otherwise subjected to physical movement that would tend to seal the lumen in the absence of said structure.

A yet still further object of the present invention is to provide a structure that serves to prevent the lumen of the extension from becoming completely closed to the flow of urine that also contains a means for wicking urine from one location to another. Said wicking means may be a part of the physical structure separate from the extension, or may be a separate physical structure attached to the tube.

A yet still further object of the present invention is to provide a system wherein all or a portion of the lumen wall of the thin-walled flat conveyance tube may be caused to have wicking properties that will enable said lumen wall to convey urine from one location to another. Said wicking properties may be formed on the tube wall through selection of a wettable material for the tube wall or by treatment of the conveyance tube wall with suitable materials.

A yet still further object of the present invention is to provide a system wherein storage of urine is accomplished by physical immobilization of liquid urine within a storage container. Said physical immobilization may be accomplished by absorption of the urine into a suitable absorbent material that is located in one or more defined areas within the storage container structure. Sufficient immobilization materials are present within the storage container to immobilize the urine conveyed to the storage container.

A yet still further object of the present invention is to provide a system wherein the physical immobilization of urine is accomplished by absorption of the urine into suitable absorbent including, but not limited to, superabsorbent polymers (SAP's), cellulose and cellulose-derived materials, and other wettable, fiberous materials including materials and structures used in wicking of urine.

A yet still further object of the present invention is to provide a system wherein the storage container has within its structure a means for distributing the urine conveyed to it to vicinity of the absorbent materials that are located in the one or more defined areas. Said distribution means may include means for distributing flow of bulk liquid urine as well as means for distribution by wicking flow A yet still further object of the present invention is to provide a system wherein the storage container is in the form of a flattened package of fixed length and width dimensions, and in which absorption of the conveyed urine will cause the package to enlarge in thickness while remaining stable in the other dimensions.

A yet still further object of the present invention is to provide a system wherein the storage container is a flattened package of fixed length and width that may be attached to or wrapped around various areas of the human body including the legs and abdominal areas using suitable means of attachment to itself, to clothing, or to the skin.

A yet still further object of the present invention is to provide a means for connecting various parts of the urine collection system wherein connection is enabled without interference to or confounding the action of wicking or separating structures within said novel means.

A yet still further object of the present invention is to provide a system wherein the storage device is a package of fixed length and width and expandable thickness that can be attached to itself, to clothing or to the human body.

A yet still further object of the present invention is to provide a system wherein the connections between the collection, conveyance, and storage means are constructed so as to provide physical contact contiguous connection of the wicking members in each of the said means so as to provide sufficient contact surface to allow wicking transfer of urine between said means. Said contact connections will allow wicking transfer of urine from said novel collection means to said novel storage means without the need to form drops or streams or other physical forms of free liquid urine to accomplish conveyance of urine at any point within said system.

Additional objects, advantages, and other novel features of the invention will be set forth in part in the description that follows and in part will become apparent to those skilled in the art upon examination of the invention. The objects and advantages of the invention may be realized and obtained by means of the instrumentalities and combinations particularly pointed out in the appended claims.

BRIEF DESCRIPTION OF THE SEVERAL VIEWS OF THE DRAWING

FIGS. 2A, 2B and 2C are front, side, standing and seated views of the female urine management system in use.

FIG. 3 is a semi-transparent view of the conveyance tube with tube lumen and spacer in normal and kinked conditions.

DETAILED DESCRIPTION OF THE INVENTION

Figure 1:
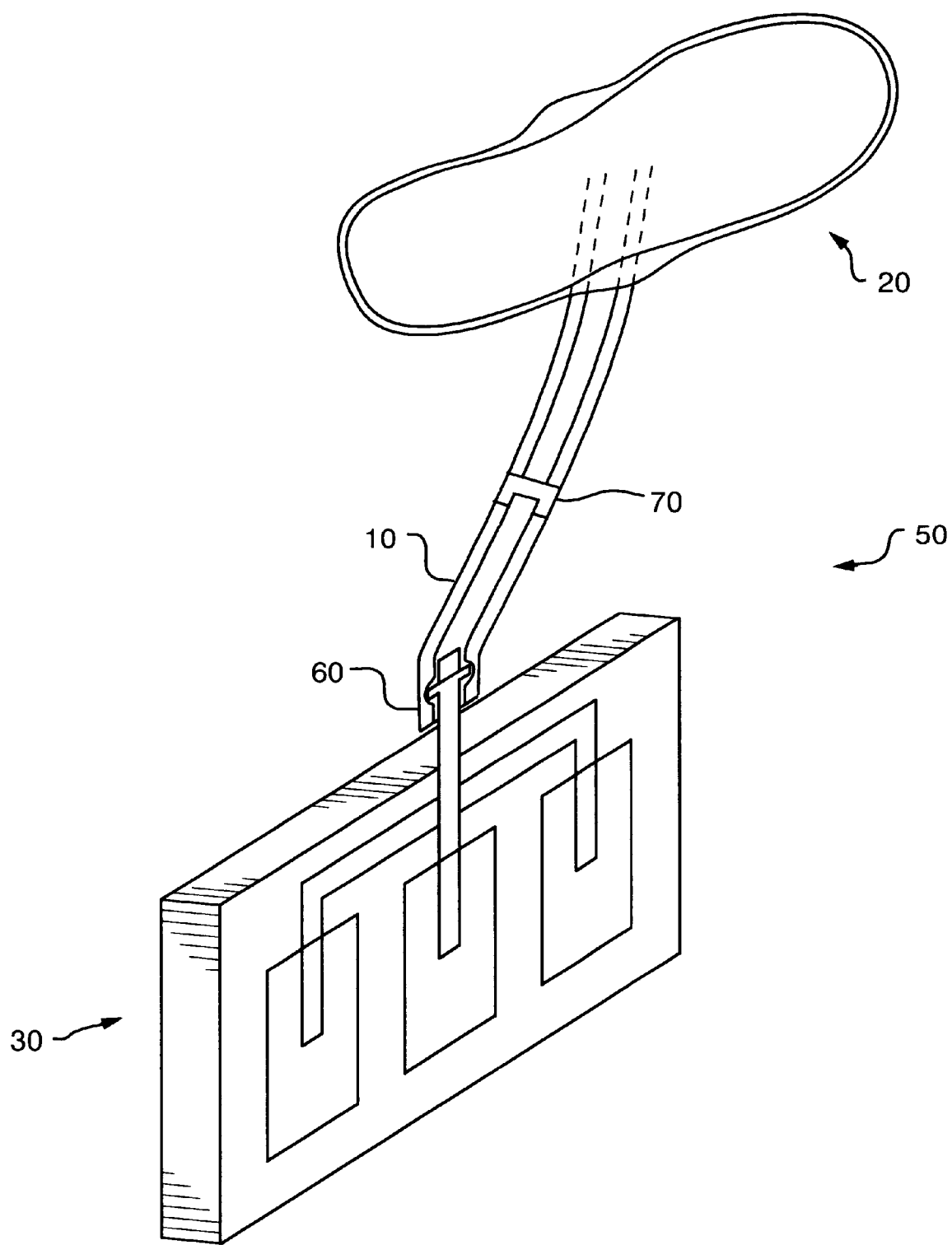
FIG. 1 is a semi-transparent, diagrammatic view of the major parts of the invention.
Figure 10:
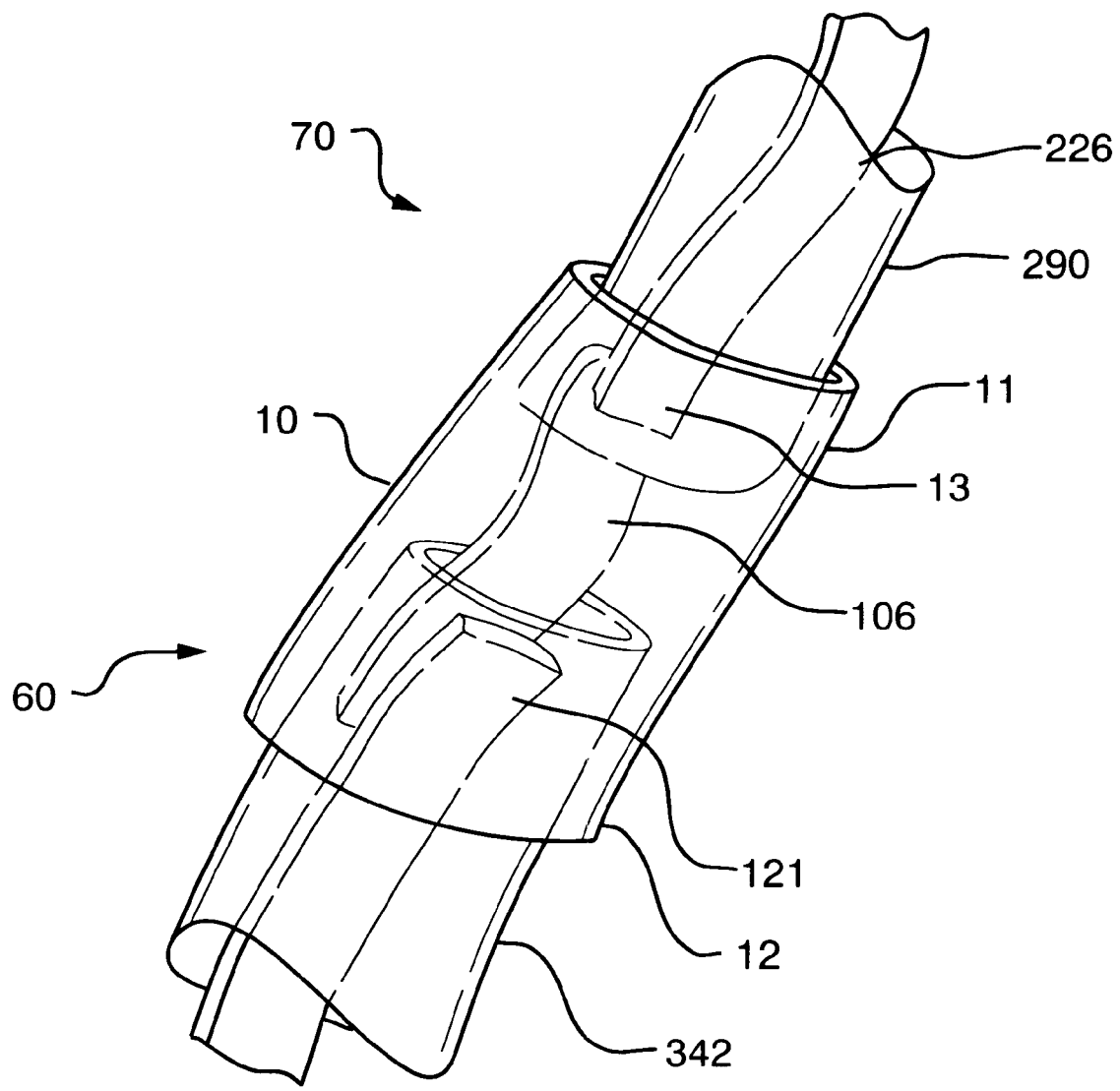
FIG. 10 is a transparent view of the continuous wicking pathway between the collection device extension and the conveyance tube.

Referring to FIGS. 1, 2c, and 10, novel urine management system 50 comprises urine collection device 20 for human females that collects and transfers urine to a urine conveyance tube 10, which conveys urine to a urine storage device 30 wherein the urine is converted to and stored in immobilized form prior to disposal. All three components of system 50 are serially connected as in FIG. 1, i.e. urine collection device 20 is connected to urine conveyance tube 10 through connection mechanism 70, and urine conveyance tube 10 is connected to urine storage device 30 through connection mechanism 60. Connection mechanisms 60 and 70 between devices 10, 20, and 30, in combination with wettable-wall and wicking transport means within each device enables the creation, within urine management system 50, of a continuous path of wicking transport that facilitates siphoning drainage from the collection site to the storage device, including when conveyance tube 10 is upgradient 120 of collection device 20 as shown in FIG. 2C. Such liquid-continuous pathways also provide the fluid source for wicking of urine by capillary-filling action to storage device 30 in locations that are higher than collector 20. By absorbing or gelling the urine within storage device 30, the head pressure of free liquid is decreased sufficiently so that the liquid will not drain back to collector 20. The wicking action also collects and removes to storage those isolated residual pools of urine which might otherwise remain in urine collector 20 or urine conveyance tube 10 to cause health and skin problems for the user.

Devices 10, 20, and 30 are independent components, and can be disassembled and reassembled replacing only those used or spent components that require replacement for proper functioning of the system. Under most conditions of use of the female urine collector that require wicking to convey the collected urine, it is necessary to use a conveyance tube with wicking capability such as described in this invention. In certain instances, where the user is heavily incontinent, thus having a urine flow profile of frequent small volumes, and where she remains in an upright (standing) position, it may be possible for her to use a conventional rubber or polymer connecting tube and a conventional storage or leg bag. In such cases, connection of the collector 20 to conventional rubber tubing and a conventional storage bag can be accomplished by means of special connecting devices to replace connecting devices 60 and 70.

Referring now to FIGS. 2A, 2B and 2C, in the preferred embodiment, which is for ambulatory, incontinent human females, urine collection device 20, held in position by undergarment 80, is connected to urine storage device 30 via flexible, thin-wall flat conveyance tube 10. Urine storage device 30 is initially in a flattened state. Urine management system 50 allows for collection of liquid urine from incontinence leakage into urine collection device 20, conveying that urine through conveyance tube 10 flowing under wicking action and gravitational influence, and then absorbing and storing the urine in immobilized form in urine storage device 30 for ultimate disposal of the device and contained urine as solid waste.

Referring now to FIG. 10, the separate connections 11/290 and 12/342 between devices 20 and 10, and between devices 10 and 30, respectively, may either be removable/re-formable or permanent. Urine collection device 20 is shown as removably affixed to one end of conveyance tube 10 by means of the combination of collector-conveyance connector 290, collection-contiguous wick connection 13, and conveyance-collector connector 11, all within the region comprising connector 70. Likewise, conveyance tube 10 is shown as removably connected to urine storage device 30 through the combination of conveyance-storage connector 12, contiguous wick connection 121, and storage-conveyance connector 342, all within the region comprising connector 60. While FIGS. 1, 2, 3, 9 and 10 show connections 60 and 70 as tubular shapes that are round in cross-section, it will be clear to those skilled in the art, that connections 60 and 70 may constructed in many shapes, including but not limited to straight, tapered, convoluted, etc, and cross-sectional geometries, including but not limited to round, oval, rectangular, polygonal, etc, so as to enable a wide variety of connection geometries. Likewise, it will also be clear to those skilled in the art, that these varieties in shape and cross-section also enable mating of the separate connections to be concave, convex, or even more-or-less flat. While not shown, it will also be clear to those skilled in the art that there are a wide variety of securing devices that can be attached to said connection components and then interlocked with a complementary securing device on the mating connection component so as to minimize the risk of the connection becoming opened or removed by accident. Connections 60 or 70 may be constructed to form a permanent connection, to be made either during fabrication or by action of the user. Thus, urine management system 50 can be formed by removably connecting separate devices 20, 10, and 30, or by removably connecting combined collector-conveyance device 20–10 with storage device 30, or by removably connecting collection device 20 with combined conveyance-storage device 10–30, by removably connecting collection device 20 with storage device 30.

Figure 7A:
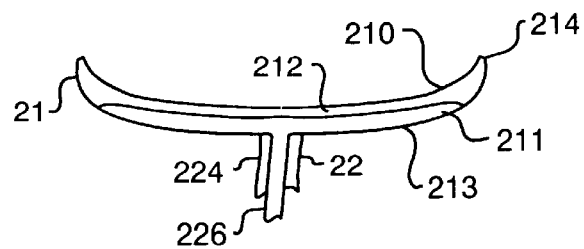
FIGS. 7A and 7B are cross-sectional views of cross-sections a–a' and b–b', respectively, shown in FIG. 8, of the collection device.
Figure 7B:
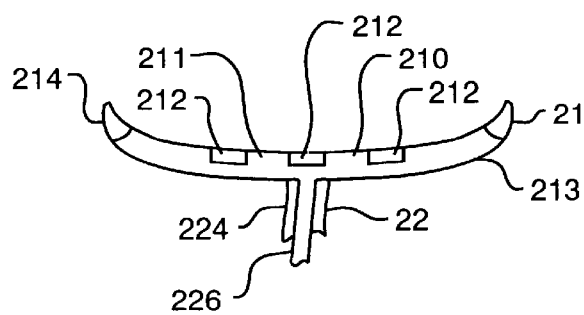
Figure 7C:
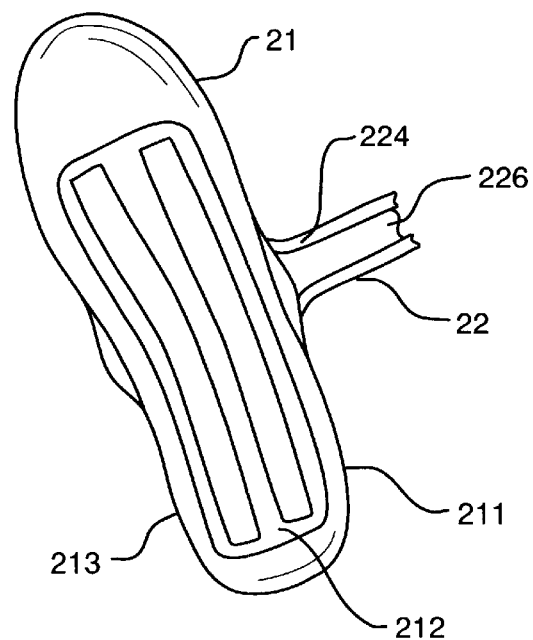
FIG. 7C is a transparent view of the collection device.

Referring to FIGS. 7A, 7B, 7C, 8, and 9, urine collection device 20 comprises a thin-wall flexible structure 21 for collecting urine from the wearer and extension 22 that incorporates spacer 226 to conduct urine from within structure 21 to collector-conveyance connector 290. Flexible structure 21 is comprised of a skin-contact surface 210 with underlying regions of wicking materials 211 that may incorporate interspersed and possibly interconnected open channels 212 that directly contact the underside of skin-contact surface 210 and that are also in contact, on one or more walls, with the wicking materials 211. Transport of urine is accomplished via capillary wicking flow through wicking materials 211, supplemented as needed by bulk fluid flow, or transitory retention, of excess urine in open channels 212 or in wicking materials 211. While FIGS. 7B and 7C show three open channels 212, it should be understood that such channels may be present in any number, or may be absent, depending upon the volume-time profile for urine flow that the particular collector is intended to accommodate.

Figure 9:
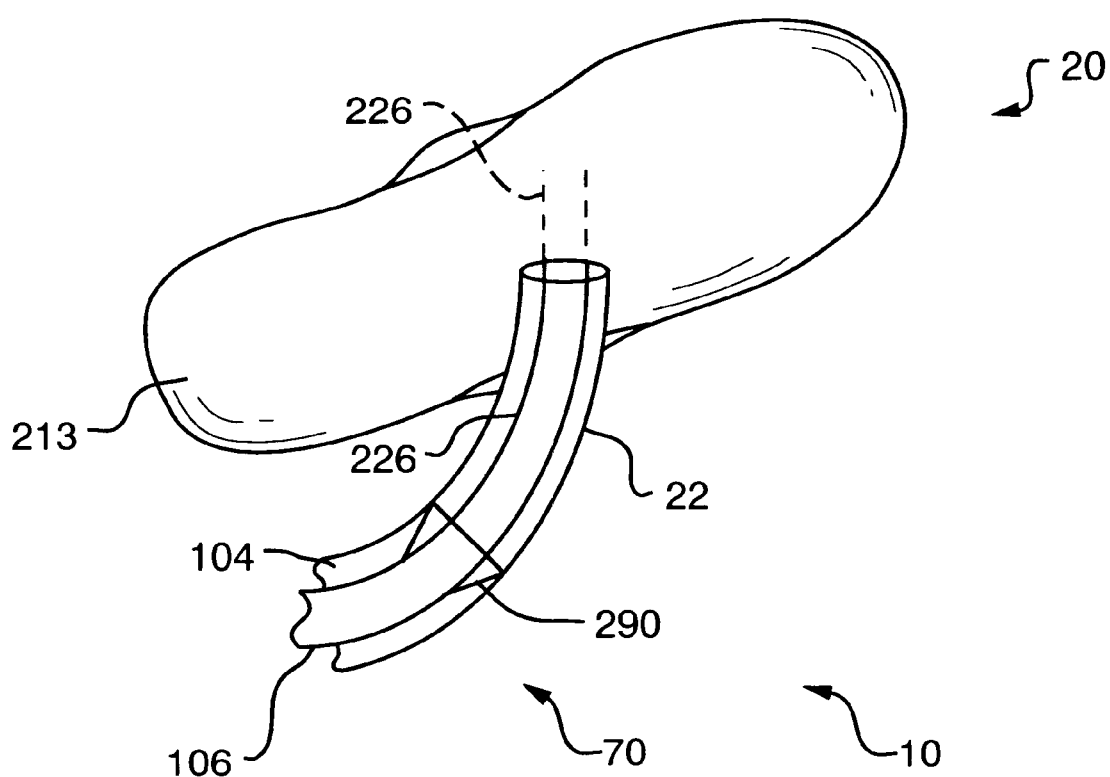
FIG. 9 is a view of the outer surface of the collection device and the extension.

Collector flexible structure 21 has a water-impermeable liquid containment layer 213 located either on its outer surface, as shown in FIGS. 7A, 7B, and 9, or between its outer surface and the active urine collection and transport region containing the wicking materials 211. Said water impermeable layer serves to prevent leakage of urine through the outer layers of the collection device.

Figure 8:
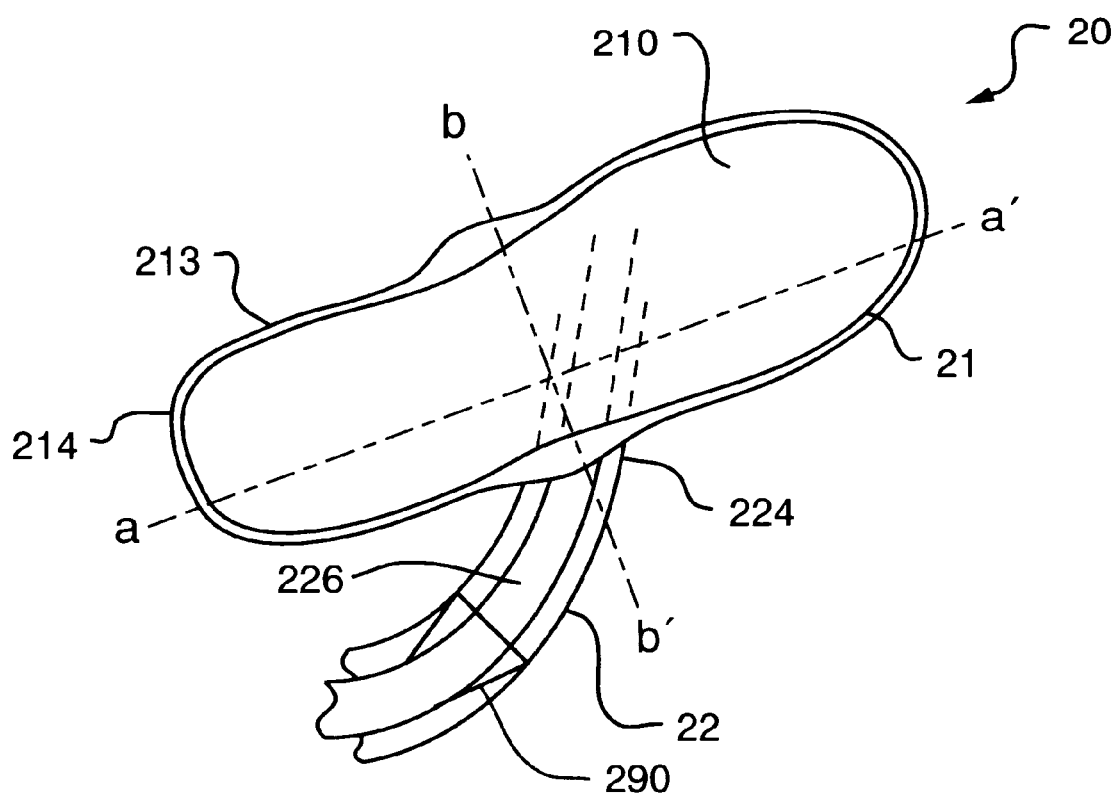
FIG. 8 is a perspective view of the skin-contact surface of the collection device.

Referring to FIGS. 7A, 7B, and 8, skin-contact surface 210 is formed from one or more layers of urine-permeable materials that allow easy passage of urine through to underlying wicking material 211 and open channels 212. Surface 210 is sufficiently pliant so that it will conform to the anatomical surface contours of the wearer's body to an extent sufficient to enable removal, by capillary pickup and wicking action, of droplets or films of liquid urine that may be transferred to one or another of the skin surfaces in the anatomical region during a urine voiding or leakage incident. Urine-impermeable barrier 214 on the perimeter of structure 21 is comprised of one or more pliant urine-impermeable materials that will conform to the contours of the skin so as to provide a barrier to the leakage of urine out of the collector region before all of the urine can be transferred through contact surface 210. Urine-impermeable barrier 214 may also be formed by coating the outer edge of structure 21 with a water-impermeable coating that will penetrate the depth of contact surface 210 at the perimeter, thus blocking outward wicking flow within structure 21, and that can also be sufficiently physically stable so as to permit formation of physical structure above contact surface 210 at barrier 214.

FIG. 9 shows the exterior surface, opposite the body-contact surface, of collector structure 21. Thin-wall extension 22 is attached to the liquid containment layer 213 in a way that assures a waterproof seal, such as adhesive or heat bonding. Spacer 226 is continuous, in the preferred embodiment, under liquid containment layer 213 in contact with the adjacent wicking materials 211 in order to assure a good wicking path. However, it should be understood that such wicking connections can be accomplished by interposition of added pieces of wicking materials in contiguous, fluid-transfer contact with each other.

In addition to providing wicking conduction of urine within thin-wall extension 22, spacer element 226 also serves to prevent complete closure of the lumen of extension 22 and resulting blockage of urine flow by crimping actions such as might occur from leg movement or from entrapment under elasticized edges of undergarments 80. This action and role of spacer 226 is analogous to that of spacer 106 in conveyance tube 10.

In the preferred embodiment, conveyance tube 10 and collector extension 22 both comprise waterproof tube film layers 104 and 224, respectively, that can easily conform to varied and changing contours and shapes, and that can be made from thin-walled plastic film, e.g. 2-mil polyethylene.

Referring now to FIG. 3, conveyance tube spacer 106 spans continuously along the length of the lumen of conveyance tube 10 to prevent tube 10 from becoming blocked to urine flow when opposite sides of wall 104 are pressed together by an external force in a crimped or kinked position 202. Presence of conveyance tube spacer 106 prevents full and complete closure of internal wall surfaces of tube wall 104 leaving enough tube opening area 102 to allow the expected fluid flow to pass. Conveyance tube spacer 106 provides an effectively continuous barrier to wall sealing along the length of tube 10, and may have the same or a variety of different cross-sectional shapes along that length. In the preferred embodiment, conveyance tube spacer 106 is constructed of a material that wicks urine, and that is flexible to allow conformance to anatomical contours, is of low density so as not to add substantial weight to extension 22, has an open, porous internal structure or a high external surface roughness that will result in a porous leaky seal even when pressed against the internal surfaces of tube 10, and is relatively more wettable by urine than polyolefins, so as to enable urine to wet the surfaces and to flow within the interstices of spacer 106.

Conveyance tube spacer 106 may be made in several forms and from a variety of materials: from aggregates of fibrous materials that derive their physical stability from the aggregation (for example, single component or blended fibers of wool, cotton, rayon, nylon, polyester, etc, in the forms of yarns, woven fabrics, mats or felts); from open-cell foamed polymers and elastomers that are wetted by aqueous fluids and that derive their physical stability from the polymer network (for example, polyurethane foams); from open-mesh materials that derive their physical stability from the strength of the individual bound fibers (for example, fibrous mats or masses, meshes and "fiber pads" of synthetic polymers such as polypropylene, and nylon, or of metals such as steel "wool"); or from flexible solids (for example, rubbery polymers such as latex and silicone rubbers). In the preferred embodiment, conveyance tube spacer 106 is made of a material with wicking properties, is capable of conveying and guiding the flow of liquids such as urine that wet those materials and fill the capillary spaces between the fibers or foam cell walls, and has sufficient physical strength to resist compression by an external force that would diminish the flow in spacer 106 to an unacceptably low rate for the intended usage. Thus, in one embodiment, conveyance tube spacer 106 is constructed of rayon felts with a width from approximately 15 to 50 mm (0.6 to 2 inch) and a thickness from approximately 2.54 to 5.08 mm (0.1 to 0.2 inch), while in another embodiment, spacer 106 is constructed of bonded cellulose acetate fiber bundles. In a third embodiment, spacer 106 is constructed of nylon mesh in different thickness. Also in the preferred embodiment, the inner surface of conveyance tube film layer 104 is either formed from materials that are inherently urine-wettable or have been subjected to surface treatments to render the inner surface wettable for holding liquid.

Referring now to FIGS. 2C and 3, conveyance tube spacer 106 allows fluid to be wicked upgradient 120 to an anatomical region which is higher than urine collection device 20, from which point the fluid can then flow down to storage device 30 which is at a point that is lower than urine collection device 20, thus forming a gravity-driven siphon flow arrangement. Spacer 106 provides the wicking pathway, even when tube 10 is kinked 202.

Figure 4:
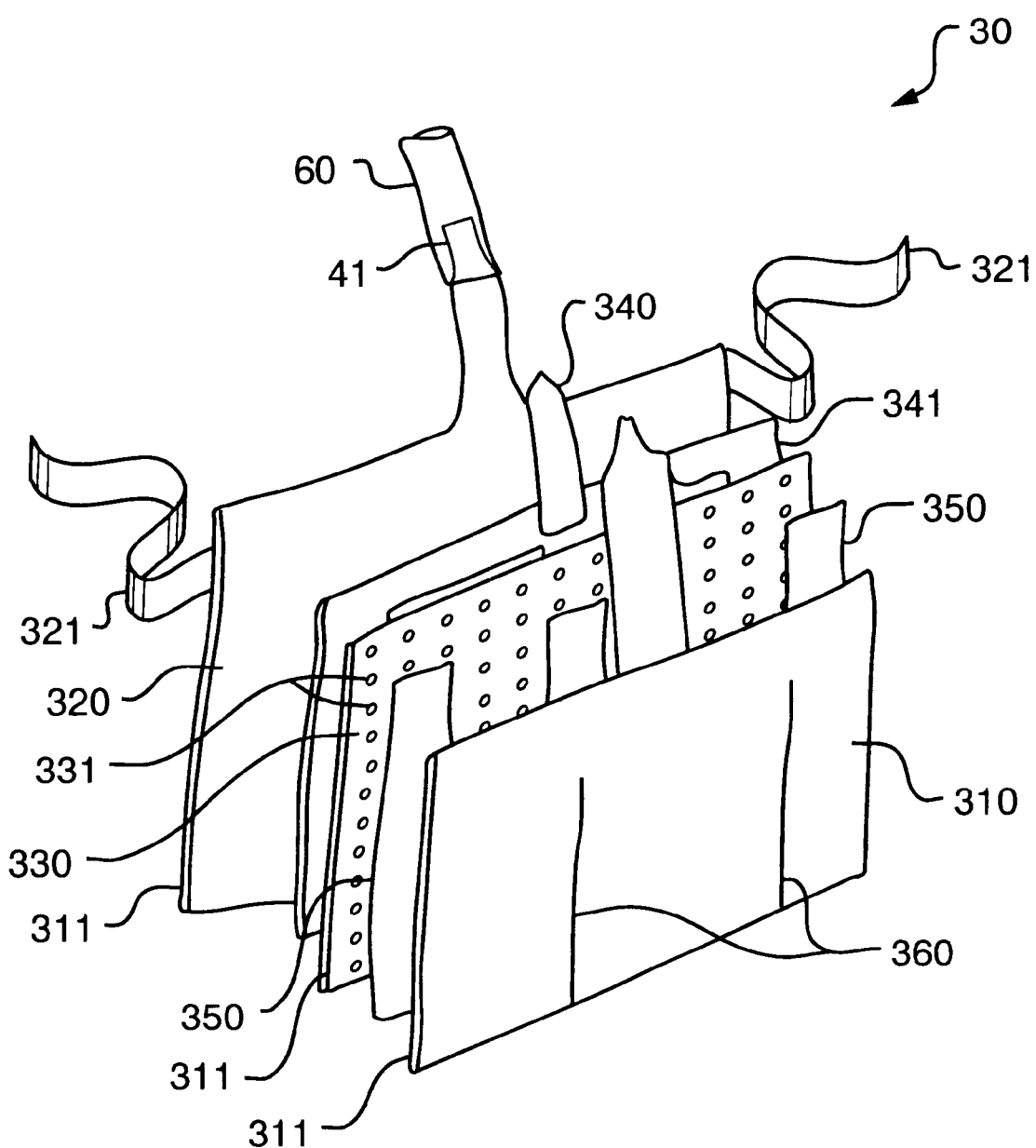
FIG. 4 is a layered view of the parts of the storage container in position relative to each other.
Figure 5:
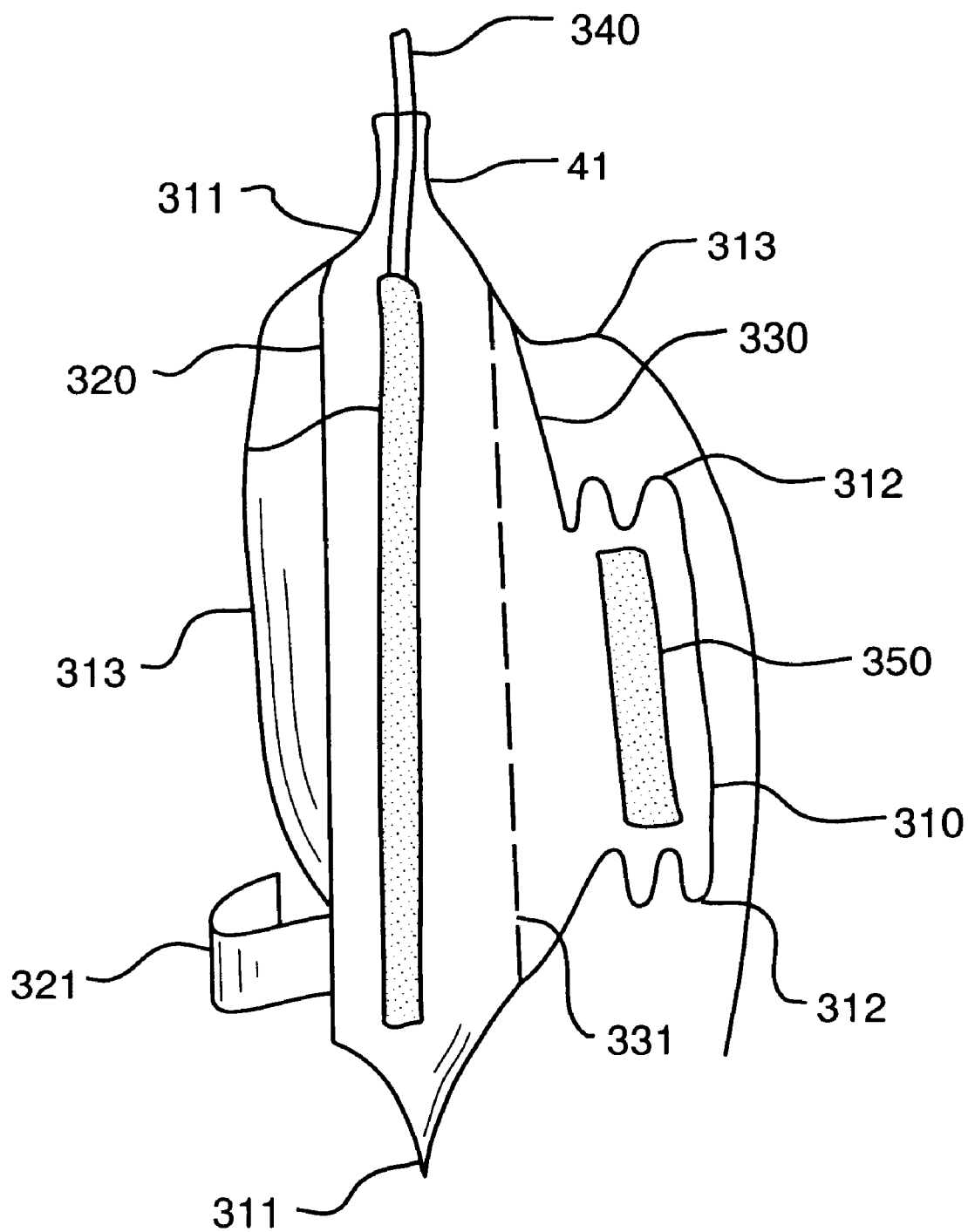
FIG. 5 is a side cross-sectional view of the storage container.
Figure 6:
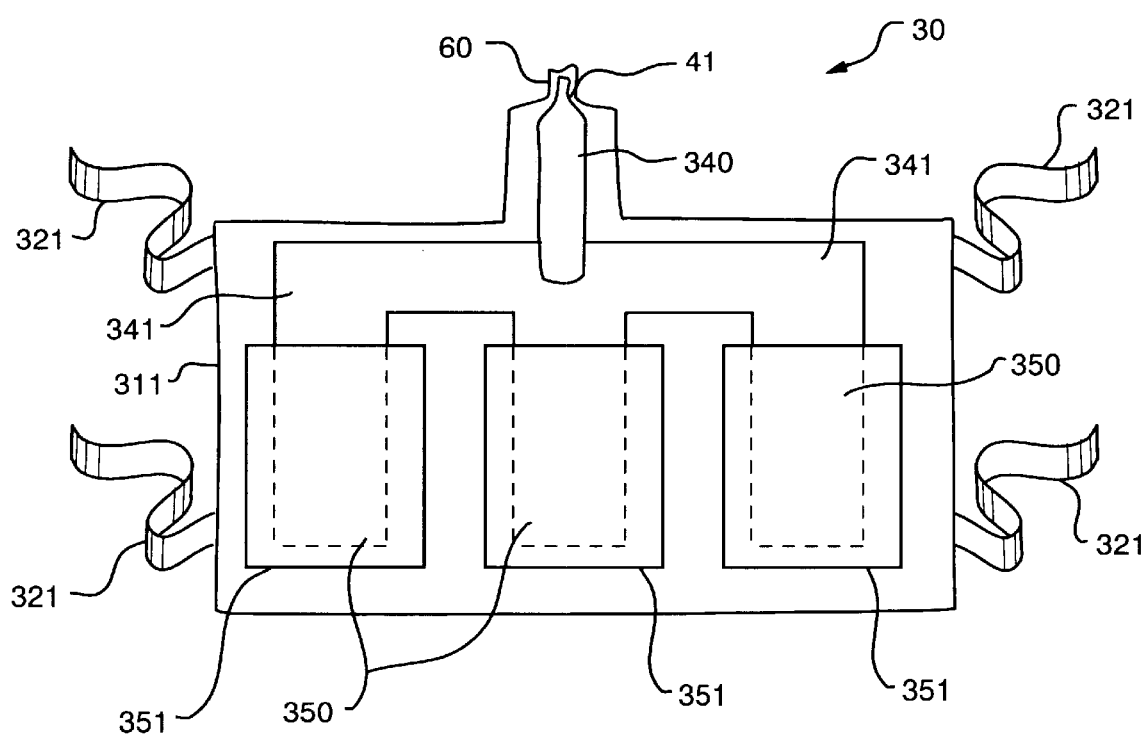
FIG. 6 is a transparent front view of the interior of the storage container.

Referring now to FIGS. 4, 5, and 6, in the preferred embodiment, urine storage device 30 comprises at least one each of urine distributor 341, liquid barrier wall 330 that has some regions of liquid permeability, and an absorbent material 350, all in contiguous fluid contact when liquid is conveyed along spacer 340. Components 341, 330, and 350 are contained within a structure formed by sealing a liquid-impervious back wall 320 and liquid-impervious front wall 310 along their peripheral edges 311 except in the vicinity of conveyance tube- storage device connector 60. Peripheral edges 311 are sealed using adhesive or heat-sealing bonding techniques that are well known in the art.

Urine storage device 30 may comprise one or more than one compartment that contains urine distributor 341, liquid permeable barrier wall 330, and absorbent materials 350 by forming walls and edges that partially enclose the compartment. In FIGS. 4 and 6, storage device 30 is shown with three compartments delineated by compartment-defining lines 360.

In the preferred embodiment for urine storage device 30, back wall 320 and front wall 310, both fabricated from thin, waterproof polymer film materials such as polyolefins, are sealed around their periphery edges 311 by thermal or adhesive edge seals, except at conveyance tube-storage device connector region 60, to form a complete, liquid-impervious outer shell. Back wall 320, barrier wall 330, and front wall 310 also can be sealed along compartment-defining lines 360 which cause the absorption and storage region to be divided into multiple compartments that are connected by spacer 340. In an embodiment with a single compartment, seal lines 360 will not be present.

As illustrated in FIG 5, front wall 310 can be either cut large or have extra wall material added to it, said extra materials being folded in at their peripheral edges 311, to permit the compartment volume to expand when liquid absorption occurs.

It should be understood that there may be additional wall structures 313, which are exterior to the urine-impervious front wall 310 or back wall 320 of urine storage device 30, said exterior walls being added for various purposes such as to aid resistance to tearing or puncturing of said walls, to provide surface comfort for the wearer, or for decorative purposes. Since such added walls are not intended to contact the conveyed or stored urine, they do not need to be liquid impermeable or to be attached with a liquid-tight seal in order for them to function.

Storage device barrier wall 330 is a liquid-impervious wall of thin polymer film, or of materials that are semi-permeable to urine, and that is located between storage device front wall 310 and back wall 320. Wall 330 is sealed to one or both of the back 320 and front walls 310 along the edges of wall 330 and along compartment defining lines 360. Storage device barrier wall 330 can comprise a thin urine-impervious film that is perforated with as few as one or an array of barrier wall holes 331 of sufficient size and number to afford the desired flow of urine through the barrier in a pattern that results in a more or less uniform wetting of absorbent array 350. Urine distributor 341 is a capillary wicking material located between back wall 320 and barrier wall 330, spacer 340, located between urine distributor 341 and connector 41, and continuing into connector 41 to provide wicking connection with conveyance device 10, may be a continuation of urine wicking distributor 341 or may be a separate piece of a wicking spacer material that is located in wicking contact with wicking distributor 341 and that provides a good wicking path from spacer 106 to distributor 341. A liquid-continuous path of wick material is present from tube-storage device connector region 60 to lower edges 351 of absorbent material 350 of urine storage device 30.

Absorbent material 350 is located in each of one or more separate compartments in urine storage device 30 in contact with the fluid passage points 331 or permeable surfaces of barrier wall 330 in order to facilitate uniform distribution of absorbed urine. Absorbent material 350 may be fixedly or removably attached to urine storage device 30 compartment walls, or may be present as unaggregated solids within each compartment. Material 350 may be any of a variety of commercially available materials that absorb aqueous fluids, including but not limited to: gel-forming resins (for example, polyacrylamide, polyacrylic acid or its Na+ salt, polyacrylic acid grafted onto starch or its $Na^+$ salt), paper-like matrices of cellulose or other natural or synthetic fibers that may themselves be partially or wholly coated with layers or fine particles of such gel-forming resins, felts of fibers prepared by needle punch, hydroentangement, or another mechanical process, inorganic absorbents (for example, silica gel and calcium sulfate), and may be combinations of aforementioned absorbents. It will be clear to those skilled in the art that there are a wide variety of absorbent materials that fall within the spirit of the invention. Absorbent materials may also include physical adsorbents such as capillary wicking materials that attract and hold liquids in their interstitial volume.

Referring now to FIGS. 2, 4, 5, and 6, for attachment of urine storage device 30 to the human body, the device can be folded around the contour of a limb, for example, the calf, with back wall 320 toward the calf, and secured in place by using leg straps 321 to complete encirclement of the limb with subsequent removable attachment to the opposite strap or to the front wall 310 using adhesive, hook and loop or other fastening means affixed to strap 321. Storage device 30 can likewise be attached to other contoured body regions such as the hip by using encircling the waist with somewhat longer straps, or can be attached to an article of user's clothing such as underpants. Storage device 30 can also be attached to fixtures or even furniture near to the user, such as a chair or wheelchair, when the user will be remaining in that place for some time period. It should be clear that there are many such attachment positions that will be convenient for the range of potential users.

Each of storage device 30, conveyance tube 10, and collector 20 contains a spacer component throughout the working length of the lumen of the device—spacer elements 211 and 226 in collection device 20, conveyance tube spacer 106 in conveyance tube 10, and storage spacer 340 and urine distributor 341 in storage device 30. When the devices 10, 20; and 30 are serially connected to form system 50, as shown in FIG. 1, then the respective spacers are brought into contiguous contact by the coupling of connectors 290 and 11 to form the collection contiguous wicking connection 13 between the spacers in the collector and conveyance device, and by coupling of connectors 12 and 342 to form the contiguous wicking connection 121 between the spacers in the conveyance device and the storage device. Said contiguous wick connections 13 and 121 are of sufficient size so that the resistance to flow across each of those contiguous contacts is not a flow-limiting point along the urine flow path. With good contiguous contact, urine that is traveling along a wick will easily bridge the gap between wicks and thus continue to move in the series-connected wicks in the same manner as if the connected ones were a single wick.

By using a material that is easily wetted by urine as the inner layer or coating on the inner layer of the collector extension 22 or the conveyance tube film layer 104, separate pools or drops of liquid urine will, upon contact with wettable surfaces, immediately wet the wettable surfaces and spread across them. When such wettable surfaces are themselves in contact with a wicking spacer, then the separate pools or drops of urine will be transferred to the wicking system and conveyed to the storage device, thereby causing the location(s) of the pools or drops to become essentially free of liquid urine. It should be noted that the skin of the urogenital region also constitutes a urine-wettable surface, and excess liquid can be wicked from skin surface.

In hydraulically connected systems, fluid flows from regions of higher to lower pressure. Hence, in a gravity-driven system, flow is from a higher physical point (i.e. higher pressure from height×density×gravitational constant) to a lower physical point (i.e., lower pressure from height× density×gravitational constant). In urine-imbibing materials such as incompletely saturated wicks and absorbents, the physical and chemical forces that hold the urine influence the relative fluid pressure; the stronger those forces, the lower the relative fluid pressure. Thus, under some conditions where the wicking and absorbent materials have absorbed only a portion of their capacity, urine can flow in an ascending path to be imbibed by the partially saturated absorbent. In the contiguously-connected urine wicking system of the instant invention, the direction and rate of flow of urine within the series-connected wicking spacers 226, 106, 340 will be governed by the relative fluid pressures of each of the hydraulically-connected streams and pockets of urine in said wicks and their associated contacting areas including the skin-contact surfaces 210 of the collection device and the contiguous skin surfaces, the surfaces of the conveyance tube film layer 104 where excess liquid urine flows, and absorbent material 350 in storage device 30. Thus, when the hydraulic pressure in storage device 30 is lower than in collector 20 or conveyance tube 10, free liquid urine can be wicked away from the urogenital vicinity and from the internal surfaces of extension 22, conveyance tube film layer 104, and storage-conveyance connector 342. In addition, of the urine present in the wicking spacers, any excess liquid urine (e.g., urine not held within capillary spaces) will be subject to hydraulically induced flow from the wicks into the lower pressure regions in absorbent material 350 within storage device 30. Thereby, any freshly-emitted incontinence leakage reaching the walls of extension 22 will be induced to flow away from the urogenital region, leaving the skin generally in a much drier state than would be experienced with prior art collection devices.

Removal of the excess liquid urine from the urogenital skin and from surfaces in collector 20 and conveyance tube 10 also reduces the volume of nutrients and fluid urine available to the various microbiological organisms that can grow and flourish in stale, standing urine. These microorganisms are frequently the source of urine decomposition products (e.g. ammonia) that are detrimental to the moist skin.

Since the wick remains wetted with urine, the possibility exists that microorganisms may grow and thus become transferable back to the user. As a means to limit the growth of undesirable microorganisms in the urine within the wick, antibacterial materials may be applied to the wick substrate as surface coatings or treatments, or may be compounded into fibers, formed into similar wicking materials and attached in contiguous contact with the wicking spacer. There are commercially available antibacterial materials whose properties are appropriate for the human contact use and that are effective against microorganisms frequently found in the urogenital region.(e.g., *Escherichia coli, Pseudomonas aeruginosa*). One example of such a commercial antibacterial material is Surfacine®, a silver-based antibacterial coating material from Surfacine Development Company, Tewksbury, Mass. To prevent growth of bacteria, collection wicking materials 211 and 226 and conveyance tube spacer 106 may be treated with antibacterial substances. The extent of the treatment region is determined by the residence time required to achieve the desired limitation and control of the target microorganisms.

The connections between devices may be fabricated so that they are permanent or are attachable/detachable to enable periodic replacement. In the preferred embodiment, nested fittings in upstream connectors 290 and 342 are the inner fittings and downstream connectors 11 and 12 are the outer fittings. Other embodiments include combinations of permanent and detachable connections among the three devices: all devices detachably connected; collector device permanently connected to conveyance device that is detachably connected to storage device; and all devices permanently connected.

Figure 11:
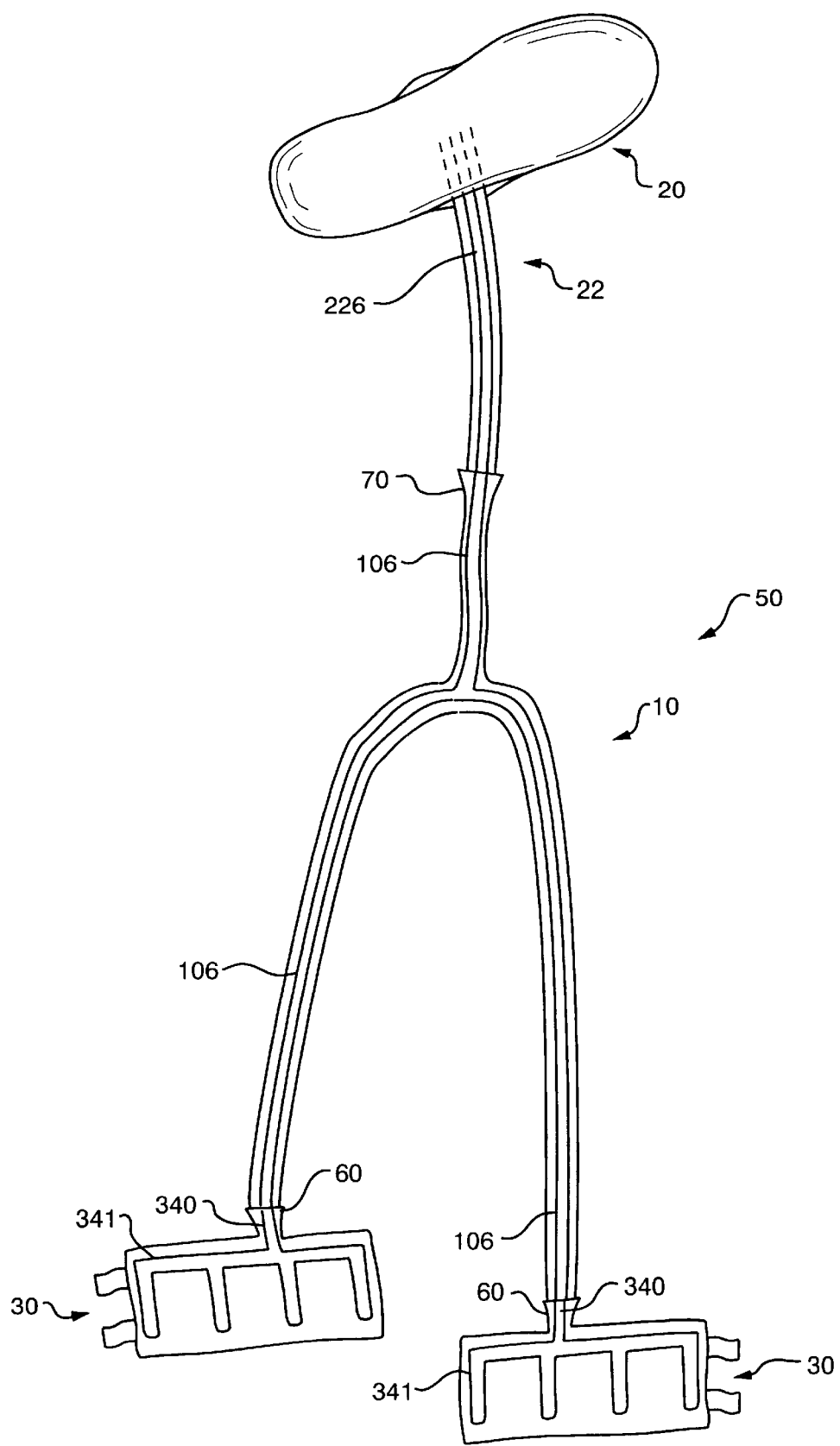
FIG. 11 is a view of the multi-output conveyance tube embodiment connected to multiple storage devices.

Referring now to FIG. 11, a variation of the preferred embodiment is shown in which conveyance tube 10 is delivering urine to multiple storage devices 30. In this embodiment, conveyance tube 10 is bifurcated to present urine to more that one storage device 30 located at different physical positions. Multiple storage devices 30 may be of different shapes and sizes from each other, and may be in different physical locations from each other, such as one attached to the user's body and one attached to or placed on a nearby piece of furniture or fixture. Such multiple connections can provide a user with convenient means to move to multiple locations and re-connect to a larger size storage device.

It is thought that the present invention and many of its attendant advantages are understood from the foregoing description. It will be apparent that various changes may be made in the form, construction, and arrangement of the parts thereof without departing from the spirit and scope of the invention or sacrificing all of its material advantages, the form hereinbefore described being merely a preferred or exemplary embodiment thereof.

We claim:

1. A system for collecting, conveying, and storing urine discharged from a human female, said system comprising:
   means for collecting urine;
   means for conveying urine, said means for conveying in fluid flow and wicking communication with said means for collecting;
   means for storing urine, said means for storing being spatially separated from said means for collection, said means for storing being in fluid flow and wicking communication with said means for conveying; and
   means for wicking urine away from the human female wherein said means for wicking moves said urine in ascending and descending flow directions, independent from movement by said human female, through said means for collection and said means for conveyance, said means for wicking depositing urine in said means for storage;
   wherein said means for collecting comprises a collection device having an inner surface and an outer structure, wherein at least said inner surface substantially conforms to contours of the human female urogenital anatomical surface where urine discharge occurs, and when said collection device is in use, said inner surface, in wicking contact with said human female surface, being capable of imbibing urine away from said human female surface, and transporting the urine from said human female surface through said inner surface and to said outer structure;
   wherein said means for conveying comprises:
      a collector extension having a first collector extension end in fluid and wicking communication with said means for collecting, said collector extension moving urine from said means for collecting to a second collector extension end of said collector extension by wicking flow and liquid flow; and a conveyance tube having a first conveyance tube end connected to said second collector extension end, and a second conveyance tube end connected to said means for storing urine, said conveyance tube including a conveyance tube means for moving urine by wicking flow and liquid flow in ascending and descending flow directions counter-gravitationally and gravitationally, independent from movement by the human female, from said means for collecting to said means for storing urine; and a urine transport and delivery pathway for achieving fluid and wicking communication between said second collector extension end and said first conveyance tube end and between said second conveyance tube end and said means for storing, wherein said urine transport and delivery pathway includes detachable connections within said urine transport and delivery pathway.

2. The system as in claim 1 wherein said urine transport and delivery pathway enables collection and transport of separate drops or pools of liquid urine from said collection device through said collector extension through said conveyance tube into said means for storing urine, said drops or pools lying either within said urine transport and delivery pathway or in wicking contact with said urine transport and delivery pathway.

3. The system as in claim 1 wherein said conveyance tube means for moving urine in ascending and descending flow directions through said conveyance tube comprises fiberous hydrophilic wicking materials that transport said urine along said means for moving by capillary wicking action.

4. The system as in claim 1 wherein the means for storing further comprises:

at least one storage device comprising:

an internal wall defining a cavity;

at least one compartment positioned within said cavity;

means for receiving urine conveyed by wicking and liquid flow into said cavity from said conveyance tube;

means for converting urine to non-liquid form within said cavity;

means for keeping separate received urine and converted non-liquid urine within said cavity; and means for distributing said received urine within said cavity.

5. The system as in claim 4 wherein said means for distributing said received urine within said cavity comprises a urine distribution channel comprising:

distribution channel means for moving urine in any direction along said distribution channel, said distribution channel means for moving selected from a group consisting of capillary wicking fluid transport forces and bulk fluid transport forces; and a urine-contact channel wall comprising at least one layer of thin film, waterproof material.

6. The system as in claim 4 wherein said means for receiving urine comprises:

an inlet opening enabling wicking and fluid communication between said conveyance tube and said storage device; and means for expansion to accommodate incoming urine.

7. The system as in claim 4 wherein said means for receiving urine comprises:

an inlet opening enabling wicking and fluid communication between said collection device and said storage device; and means for expansion to accommodate incoming urine.

8. The system as in claim 4 wherein said internal wall and said at least one compartment comprise thin films of polymeric materials wherein said internal wall has thickness in the range of 0.013 to 0.25 mm (0.0005 to 0.0 10 inch).

9. The system as in claim 4 wherein said means for keeping separate received urine and converted non-liquid urine comprises at least one of each liquid urine region and non-liquid urine region, said non-liquid urine region comprising a region interior wall and absorbent, said at least one liquid region having adjacent placement with respect to said at least one non-liquid region, and said liquid region being separated from said non-liquid region by a barrier comprising means for limiting the flow of urine from said liquid urine region through said barrier to said non-liquid urine region, and said means for converting urine to said non-liquid urine comprises said absorbent that, prior to storing urine, is physically distributed and held in pre-determined locations within said non-liquid region, said absorbent selected from a group consisting of natural fibers, synthetic fibers, cellulose fibers, water- absorbing natural materials, water-absorbing synthetic materials, and shredded paper.

10. The system as in claim 9 wherein said absorbent is selected from a group consisting of non-woven fibers, a non-woven mat of fibers, absorbent materials attached to the region interior wall, and material suitable for confining the urine by capillary force.

11. The system as in claim 9 wherein said absorbent comprises materials selected from a group consisting of hydrophilic polymers formed from a variety of synthetic polar polymeric materials, both alone and chemically combined with natural polymers including starches; inorganic compounds that react with aqueous liquids to form solid hydrate compounds including silica gel and calcium sulfate; and organic fiber masses, both woven and non-woven, including cellulose fiber.

12. The system as in claim 9 wherein said absorbent comprises materials selected from a group consisting of gel resin polyacrylamide, gel resin polyacrylic acid, $Na^+$ salt, polyacrylic acid $Na^+$ salt on starch, gel resin fine particles in paper fiber matrix, needled felt pads, absorbent paper, and gel resin with inorganic absorbent.

13. The system as in claim 9 wherein said means for limiting flow comprises piercing said barrier in an arrangement of small penetrations through which urine can travel from said liquid region to said non-liquid urine region.

14. The system as in claim 9 wherein the means for storing is reusable and comprises:

means for removing for disposal said absorbent containing said converted non-liquid urine from said means for storing; and means for refilling said means for storing with said absorbent.

15. The system as in claim 1 wherein the means for storing further comprises means for preventing urine from returning to said inner side of said collection device.

16. The system as in claim 1 further comprising a means for attaching said means for storing to a surface selected from the group consisting of a human female body, human female clothing, and human female surroundings.

17. The system as in claim 16 wherein the means for attaching is selected from the group consisting of elastic bands, woven elastomeric fabric bands, hook and loop attachment means, adhesive dots or bands, and placement within the pouch or pocket of said clothing.

18. The system as in claim 1 wherein the means for storing comprises:

at least one disposable storage container having at least one a single inlet opening through which urine flows from said conveyance tube; and means for capping said at least one single inlet opening to retain urine within said storage container.

19. The system of claim 1 wherein said means for storage comprises:
at least one container, for storing incoming urine, having an outer shell, peripheral edges, and an inlet connector, said outer shell comprising at least one layer of a urine impervious material thinner than 10 mils, said peripheral edges having liquid-tight sealing one to another, said inlet connector opening having means for expansion to accommodate incoming urine.

20. The system of claim 4 further comprising a storage device exterior wall and peripheral edges, said storage device exterior wall comprising liquid urine impervious material and said peripheral edges having liquid-tight sealing one to another.

21. The system of claim 1 wherein said means for storing urine further comprises urine-immobilizing materials that, prior to storing urine, are held in place by a matrix of material selected from a group consisting of natural fibers, synthetic fibers, cellulose fibers, water-absorbing natural materials, water-absorbing synthetic materials, and shredded paper.

22. The system of claim 1 wherein said means for storing further comprises an initially flat container that expands upon filling with urine.

23. The system as in claim 1 wherein said outer structure of said collection device comprises a waterproof, flexible surface that houses said inner surface of said collection device, said outer structure extending around a periphery of said human female surface, said outer structure effectively forming a waterproof containment region around said inner surface of said collection device and a barrier to leakage of urine from said collection device.

24. The system of claim 1 wherein said outer structure of said collection device comprises at least one layer of waterproof material.

25. The system of claim 1 wherein said collection device further comprises a urine-intake layer between said inner surface and said outer structure, said urine-intake layer including a layer of a material that is hydrophilic and that has openings that enable passage of urine from said inner surface through said urine-intake layer to said outer structure while inhibiting passage of urine in the opposite direction.

26. The system of claim 25 wherein said urine intake layer further comprises:
a capillary volume of said urine intake layer; and
at least one open channel for conducting urine, whose volume temporarily exceeds said capillary volume of said urine intake layer, to said collector extension.

27. The system of claim 1 wherein said second conveyance tube end comprises multiple, simultaneous connections to said means for storing urine.

28. The system of claim 1 further comprising:
a tube-shaped structure formed from thin-wall plastic film, said thin-wall plastic film capable of becoming flattened, including:
a waterproof outer surface;
an interior channel defined by said outer surface; and
extension means for spacing positioned within said interior channel, said extension means for spacing preventing said collector extension from crimping sufficiently to block drainage of the urine.

29. The system of claim 28 wherein said extension means for spacing comprises a spacer made from materials selected from a group consisting of loosely knitted nylon fibers, loosely knitted polyolefin fibers, flexible solid shapes of polyolefins, flexible solid shapes of silicone rubber, loosely knitted fiberglass, open-mesh metallic fibers and wools, polyethylene film, and porous wicking materials including needled felts of rayon and cellulose acetate fiber bundles, natural or synthetic woven fabrics.

30. The system of claim 1 wherein said collector extension comprises material selected from the group consisting of rubbery polymer including silicone rubber and latex rubber, elastic fabric coated with a material that prevents urine leakage, polyolefins, and flexible polymeric film materials and fabrics.

31. The system of claim 1 wherein said conveyance tube means for moving the urine further comprises wicking material selected from a group consisting of rayon acetate needled felting; single component fibers selected from a group consisting of wool, cotton, rayon, nylon, and polyester; blended fibers selected from a group consisting of wool, cotton, rayon, nylon, and polyester; said single component and said blended fibers fabricated into a form selected from a group consisting of yarns, woven fabrics, mats, and felts; open-cell foamed polymers, elastomers such as polyurethane foams; open-mesh materials such as open- mesh metallic fibers and wools; meshes of synthetic polymers such as polypropylene; and flexible solids such as latex.

32. A system as in claim 1 wherein said conveyance tube further comprises:
a tube-shaped structure formed from waterproof, thin-wall plastic film and capable of becoming flattened including:
a conveyance tube outer surface;
a conveyance tube interior channel bounded by an interior surface of said conveyance tube outer surface;
a conveyance tube means for spacing positioned within said conveyance tube interior channel, said conveyance tube means for spacing preventing said conveyance tube interior channel from crimping sufficiently to block passage of urine.

33. In a urine management system for incontinent humans comprising means for collection of urine, a means for storage of urine received from said means for collection comprising:
at least one storage container for said urine, each said at least one storage container having an outer shell and an inner cavity defined by said outer shell;
means for conveyance of urine from said collection device to said at least one storage container, said means for conveyance capable of wicking urine towards said at least one storage container, means for conveyance capable of conveying urine counter-gravitationally and gravitationally; and
means for distributed absorption of urine disposed within each said inner cavity of each said at least one storage container.

34. The means for storage of claim 33 wherein each said inner cavity of each said at least one storage container comprises at least one compartment wherein each said at least one compartment includes within it a material selected from a group consisting of polyacrylamide, polyacrylic acid: $Na^+$ salt, polyacrylic acid: Na+ salt on starch, resin fine particles in paper fiber matrix, needled felt pads, absorbent paper towels, and gel resin combined with inorganic absorbent.

35. The means for storage of claim 33 further comprising absorbent material disposed within said each said inner cavity of each said at least one storage container selected from a group consisting of super absorbent polymers, cellulose, cellulose-derived materials, and wettable, fiberous materials.

36. The means for storage of claim 33 further comprising a means for attaching each said at least one storage container to human body, clothing, or surroundings, wherein said means for attaching is selected from the group consisting of elastic bands, woven elastomeric fabric bands, hook and loop attachment means, adhesive dots or bands, and placement within the pouch or pocket of said clothing.

37. In a urine management system for human females having a urine collection device, a thin-wall conveyance tube capable of becoming flattened and forming a cavity, said cavity including means for spacing and wicking within said cavity, a collection end means for connection, and at least one storage end means for connection; means for attaching said conveyance tube to said urine collection device at collection end means for connection, at least one storage container, means for attaching said at least one storage container to or to surroundings near to the human female, means for attaching said at least one storage container to said conveyance tube at said at least one storage end means for connection, and means for presenting at least one fresh storage container, a method for use of said urine management system comprising the steps of:

attaching said urine collection device to said human;

attaching said conveyance tube to said urine collection device;

attaching said at least one storage device to or to surroundings near to said human through said means for attaching;

attaching said tube to said at least one storage container;

depositing urine into said urine collection device; and removing and replacing said at least one storage container by said means for presenting said fresh storage container when said at least one storage container is full.

38. A method as in claim 37 wherein said storage container is selected from a group consisting of disposable and reusable.

* * * * *